US008796305B2

(12) United States Patent
Vakalopoulos et al.

(10) Patent No.: US 8,796,305 B2
(45) Date of Patent: Aug. 5, 2014

(54) CARBOXY-SUBSTITUTED IMIDAZO[1,2-A]PYRIDINECARBOXAMIDES AND THEIR USE

(71) Applicant: Bayer Pharma Aktiengesellschaft, Berlin (DE)

(72) Inventors: Alexandros Vakalopoulos, Hilden (DE); Ingo Hartung, Berlin (DE); Markus Follman, Köln (DE); Rolf Jautelat, Haan (DE); Niels Lindner, Wuppertal (DE); Dirk Schneider, Wuppertal (DE); Frank Wunder, Wuppertal (DE); Johannes-Peter Stasch, Solingen (DE); Gorden Redlich, Bochum (DE); Volkhart Min-Jian Li, Velbert (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 13/789,414

(22) Filed: Mar. 7, 2013

(65) Prior Publication Data

US 2014/0128425 A1 May 8, 2014

(30) Foreign Application Priority Data

Nov. 5, 2012 (EP) .................................... 12191202

(51) Int. Cl.
*C07D 401/10* (2006.01)
*C07D 401/02* (2006.01)
*A61K 31/4353* (2006.01)

(52) U.S. Cl.
CPC ............ *C07D 401/10* (2013.01); *C07D 401/02* (2013.01); *A61K 31/4353* (2013.01)
USPC .......................................... 514/300; 546/121

(58) Field of Classification Search
CPC . C07D 401/02; C07D 401/10; A61K 31/4353
USPC .......................................... 546/121; 514/300
See application file for complete search history.

(56) References Cited

U.S. PATENT DOCUMENTS

| 5,691,336 | A | 11/1997 | Dorn et al. |
| 5,698,704 | A | 12/1997 | Jackson |
| 6,180,656 | B1 | 1/2001 | Fürster et al. |
| 8,212,041 | B2 | 7/2012 | Albrecht et al. |
| 2008/0051409 | A1 | 2/2008 | Gmeiner et al. |
| 2008/0103183 | A1 | 5/2008 | Ackermann et al. |
| 2009/0124612 | A1 | 5/2009 | Albrecht et al. |
| 2010/0092966 | A1 | 4/2010 | Burkhardt et al. |
| 2013/0203751 | A1 | 8/2013 | Hubsch et al. |

FOREIGN PATENT DOCUMENTS

| EP | 0266890 A1 | 5/1988 |
| EP | 1277754 A1 | 2/2003 |
| JP | H01258674 | 10/1989 |
| WO | 8903833 A1 | 5/1989 |
| WO | 9634866 A1 | 11/1996 |
| WO | 2008082490 A2 | 7/2008 |
| WO | 2008134553 A1 | 11/2008 |
| WO | 2010030538 A2 | 3/2010 |
| WO | 2011113606 A1 | 9/2011 |
| WO | 2011141409 A1 | 11/2011 |
| WO | 2012143796 A2 | 10/2012 |
| WO | 2012165399 | * 12/2012 |

OTHER PUBLICATIONS

Chien-nien et al., vascular pharmacology, vol. 58 (2913), pp. 211-218, (2013).*
Witte et al., "Experimental heart failure in rats: effects on cardiovascular circadianrhythms and on myocardial β-adrenergic signaling," Cardiovascular Research, 2000, 47:350-358.
Yu et al., "Vasorelaxant Effect of Isoliquiritigenin, A Novel Soluble Guanylate Cyclase Activator, in Rat Aorta," British Journal of Pharmacology, 1995, 114:1587-1594.
Dembinski et al.,"Recent Advances in the Mitsunobu Reaction: Modified Reagents and the Quest for Chromatography-Free Separation," Eur. J. Org. Chem., 2004, 13:2763-2772.
Deng et al., "Studies on Phosphoroheterocycle Chemistry II: A Simple and New Route to 1,3,2-Diazaphospholidine-4-thione 2-sulfide Derivatives," Synthesis, 2001, 16:2445-2449.
Gensini et al., "3-Azabicyclo[3.1.0]hex-1-ylamines by Ti-Mediated Intramolecular ReductiveCyclopropanation of α-(N-Allylamino)-Substituted N,N-Dialkylcarboxamidesand Carbonitriles," Eur. J. Org. Chem., 2002, 15: 2499-2507.
Glass et al., "Stimulation of Human Platelet Guanylate Cyclase by Fatty Acids," J. Biol. Chem., 1977, 252 (4):1279-1285.
Greene et al., Greene's Protective Groups in Organic Synthesis, 4th ed., chapter 1, "The Role of Protective Groups in Organic Synthesis," 2007, Published by John Wiley & Sons, New York.
Hjorringgaard et al., "An Automatic Solid-Phase Synthesis of Peptaibols," J. Org. Chem., 2009, 74:1329-1332.
Hoenicka et al., "Purified Soluble Guanylyl Cyclase Expressed in A Baculovirus/Sf9 System: Stimulation by YC-1, Nitric Oxide, and Carbon Monoxide," J. Mol. Med., 1999, 77:14-23.
Hughes et al., Organic Reactions, vol. 42, Chapter 2, 1992, 335-395 and 636-656, "The Mitsunobu Reaction," Published by John Wiley & Sons, Inc.
Kozo et al., International Review of Experimental Pathololgy, vol. 7, 1969, chapter 2, "Spontaneous Hypertension in Rats," Published by Academic Press, Inc., New York, 227-270.

(Continued)

*Primary Examiner* — Niloofar Rahmani
(74) *Attorney, Agent, or Firm* — Karen B. King

(57) ABSTRACT

The present application relates to novel substituted imidazo [1,2-a]pyridine-3-carboxamides, to processes for their preparation, to their use alone or in combinations for the treatment and/or prophylaxis of diseases and to their use for preparing medicaments for the treatment and/or prophylaxis of diseases, in particular for the treatment and/or prophylaxis of cardiovascular disorders.

6 Claims, No Drawings

(56) References Cited

OTHER PUBLICATIONS

Maarten van den Buuse, "Circadian Rhythms of Blood Pressure, Heart Rate,and Locomotor Activity in Spontaneously Hypertensive Rats as MeasuredWith Radio-Telemetry," Physiology & Behavior, 1994, 55:(4) 783-787.

McElroy et al., "The Preparation and Properties of Crystalline Firefly Luciferin," Archives of Biochemistry and Biophysics 1957, 72:358-368.

Mülsch et al., "Effect of YC-1, An NO-independent, Superoxide-senstive Stimulator of Soluble Guanylyl Cyclase, On Smooth Muscle Responsiveness to Nitrovasodilators," British Journal Pharmacology 1997, 120:681-689.

Ogrel et al., "Synthesis of 15N-Labelled D-Isovaline and á-Aminoisobutyric Acid," Eur. J. Org. Chem., 2000, 5:857-859.

Pettibone et al., "A Structurally Novel Stimulator of Guanylate Cyclase With Long-Lasting Hypotensive Activity in the Dog," European Journal of Pharmacology, 1985, 116:307-312.

Soler et al., "Betulinic Acid Derivatives: A New Class of Specific Inhibitors of Human Immunodeficiency Virus Type 1 Entry," Journal Med. Chem., 1996, 39:1069-1083.

Stasch et al., "Cardiovascular actions of a novel NO-independent guanylyl cyclase stimulator, BAY 41-8543: in vivo studies," British Journal of Pharmacology, 2002, 135(2): 344-355.

Ko et al., "YC-1, a novel activator of platelet guanylate cyclase," Blood, 1994, 84(12): 4226-4233.

Wunder et al., "A cell-based cGMP assay useful for ultra-high-throughput screening and identification of modulators of the nitric oxide/cGMP pathway," Analytical Biochemistry, 2005, 339:104-112.

U.S. Appl. No. 13/789,655, filed Mar. 7, 2013.
U.S. Appl. No. 14/071,274, filed Nov. 1, 2013.
U.S. Appl. No. 13/789,208, filed Dec. 11, 2013.
U.S. Appl. No. 14/071,274, filed Nov. 4, 2013.

Lasker et al., "Targeting soluble guanylate cyclase for the treatment of pulmonary hypertension," Expert Rev Respir Med., Apr. 2011, 5:(2)153-161.

* cited by examiner

CARBOXY-SUBSTITUTED IMIDAZO[1,2-A]PYRIDINECARBOXAMIDES AND THEIR USE

The present application relates to novel substituted imidazo[1,2-a]pyridine-3-carboxamides, to processes for their preparation, to their use alone or in combinations for the treatment and/or prophylaxis of diseases and to their use for preparing medicaments for the treatment and/or prophylaxis of diseases, in particular for the treatment and/or prophylaxis of cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory site. The latter is of central importance for the mechanism of activation. NO is able to bind to the iron atom of haem and thus markedly increase the activity of the enzyme. Haem-free preparations cannot, by contrast, be stimulated by NO. Carbon monoxide (CO) is also able to attach to the central iron atom of haem, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, myocardial infarction, thromboses, stroke and sexual dysfunction.

A possible way of treating such disorders which is independent of NO and aims at influencing the cGMP signaling pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of haem. Besides the side effects, the development of tolerance is one of the crucial disadvantages of this mode of treatment.

Over the last years, a number of substances which stimulate soluble guanylate cyclase directly. i.e. without prior release of NO, have been described, for example 3-(5'-hydroxymethyl-2'-furyl)-1-benzylindazole [YC-1; Wu et al., Blood 84 (1994), 4226; Mülsch et al., Brit. J. Pharmacol. 120 (1997), 681], fatty acids [Goldberg et al., J. Biol. Chem. 252 (1977), 1279], diphenyliodonium hexafluorophosphate [Pettibone et al., Eur. J. Pharmacol. 116 (1985), 307], isoliquiritigenin [Yu et al., Brit. J. Pharmacol. 114 (1995), 1587], and also various substituted pyrazole derivatives (WO 98/16223).

EP 0 266 890-A1, WO 89/03833-A1, JP 01258674-A [cf. Chem. Abstr. 112:178986], WO 96/34866-A1, EP 1 277 754-A1, WO 2006/015737-A1, WO 2008/008539-A2, WO 2008/082490-A2, WO 2008/134553-A1, WO 2010/030538-A2 and WO 2011/113606-A1, inter alia, describe various imidazo[1,2-a]pyridine derivatives which can be used for treating disorders.

It was an object of the present invention to provide novel substances which act as stimulators of soluble guanylate cyclase and, as such, are suitable for the treatment and/or prophylaxis of diseases.

The present invention provides compounds of the general formula (I)

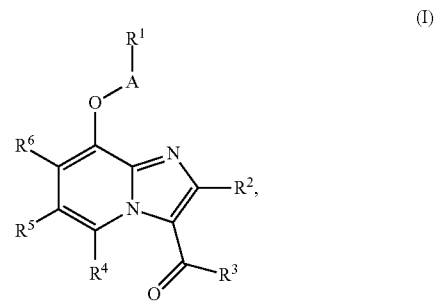

in which

A represents $CH_2$, $CD_2$ or $CH(CH_3)$, $R^1$ represents $(C_4-C_6)$-alkyl, $(C_3-C_7)$-cycloalkyl or phenyl,
    where $(C_4-C_6)$-alkyl may be substituted up to six times by fluorine,
    where $(C_3-C_7)$-cycloalkyl may be substituted by 1 to 4 substituents independently of one another selected from the group consisting of fluorine, trifluoromethyl and $(C_1-C_4)$-alkyl,
    and
    where phenyl may be substituted by 1 to 4 substituents independently of one another selected from the group consisting of halogen, cyano, monofluoromethyl, difluoromethyl, trifluoromethyl, $(C_1-C_4)$-alkyl, $(C_1-C_4)$-alkoxy, difluoromethoxy and trifluoromethoxy, $R^2$ represents hydrogen, $(C_1-C_4)$-alkyl, cyclopropyl, monofluoromethyl, difluoromethyl or trifluoromethyl, $R^3$ represents a group of the formula

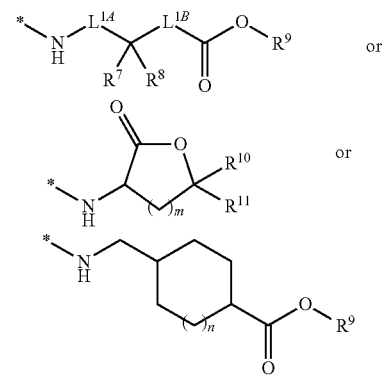

where
* represents the point of attachment to the carbonyl group,
$L^{1a}$ represents a bond or $(C_1-C_4)$-alkanediyl,
    where $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy, $L^{1B}$ represents a bond or $(C_1-C_4)$-alkanediyl,
where $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy, $R^7$ represents hydrogen, $(C_1-C_6)$-alkyl, $(C_2-C_6)$-alkenyl, $(C_2-C_6)$-alkynyl, $(C_3-C_7)$-cycloalkyl, 5- or 6-membered heteroaryl or phenyl,
where $(C_1-C_6)$-alkyl may be substituted by 1 to 3 substituents independently of one another selected from the group consisting of fluorine, trifluoromethyl, difluoromethoxy, trifluoromethoxy, hydroxy, $(C_1-C_4)$-alkoxy, phenyl, phenoxy and benzyloxy,
where phenyl, phenoxy and benzyloxy for their part may be substituted by 1 or 2 halogen substituents,
where $(C_3-C_7)$-cycloalkyl may be substituted by 1 or 2 substituents independently of one another selected from the group consisting of fluorine, trifluoromethyl, $(C_1-C_4)$-alkyl and $(C_1-C_4)$-alkoxy,
and
where phenyl and 5- or 6-membered heteroaryl may be substituted by 1 to 3 substituents independently of one another selected from the group consisting of halogen, cyano, trifluoromethyl, $(C_1-C_4)$-alkyl, $(C_1-C_4)$-alkoxy and $(C_1-C_4)$-alkylsulphonyl, $R^8$ represents hydrogen or $(C_1-C_4)$-alkyl,
or
$R^7$ and $R^8$ together with the carbon atom to which they are attached form a 3- to 7-membered carbocycle or a 4- to 7-membered heterocycle,
where the 3- to 7-membered carbocycle and the 4- to 7-membered heterocycle may be substituted by 1 to 3 substituents independently of one another selected from the group consisting of fluorine and $(C_1-C_4)$-alkyl, $R^9$ represents hydrogen or $(C_1-C_6)$-alkyl,
$R^{10}$ represents hydrogen or $(C_1-C_4)$-alkyl,
$R^{11}$ represents hydrogen or $(C_1-C_4)$-alkyl,
m represents 1, 2 or 3,
n represents 0, 1 or 2,
$R^4$ represents hydrogen,
$R^5$ represents hydrogen, halogen, cyano, difluoromethyl, trifluoromethyl, $(C_1-C_4)$-alkyl, $(C_3-C_7)$-cycloalkyl, $(C_2-C_4)$-alkynyl, difluoromethoxy, trifluoromethoxy or $(C_1-C_4)$-alkoxy,
$R^6$ represents hydrogen or halogen,
and their N-oxides, salts, solvates, salts of the N-oxides and solvates of the N-oxides and salts.

Compounds according to the invention are the compounds of the formula (I) and their salts, solvates and solvates of the salts, the compounds included in the formula (I) of the formulae mentioned in the following and their salts, solvates and solvates of the salts, and the compounds included in the formula (I) and mentioned in the following as embodiment examples and their salts, solvates and solvates of the salts, where the compounds included in the formula (I) and mentioned in the following are not already salts, solvates and solvates of the salts.

Preferred salts in the context of the present invention are physiologically acceptable salts of the compounds according to the invention. Salts which are not themselves suitable for pharmaceutical uses but can be used, for example, for isolation or purification of the compounds according to the invention are also included.

Physiologically acceptable salts of the compounds according to the invention include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid, and benzoic acid.

Physiologically acceptable salts of the compounds according to the invention also include salts of conventional bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanol-amine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are designated as those forms of the compounds according to the invention which form a complex in the solid or liquid state by coordination with solvent molecules. Hydrates are a specific form of solvates, in which the coordination takes place with water. Hydrates are preferred solvates in the context of the present invention.

The compounds according to the invention can exist in different stereoisomeric forms depending on their structure, i.e. in the form of configuration isomers or optionally also as conformation isomers (enantiomers and/or diastereomers, including those in the case of atropisomers). The present invention therefore includes the enantiomers and diastereomers and their particular mixtures. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention can occur in tautomeric forms, the present invention includes all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2H$ (deuterium), $^3H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^3H$ or $^{14}C$ isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by processes known to those skilled in the art, for example by the methods described below and the methods described in the working examples, by using corresponding isotopic modifications of the particular reagents and/or starting compounds therein.

The present invention moreover also includes prodrugs of the compounds according to the invention. The term "prodrugs" here designates compounds which themselves can be biologically active or inactive, but are converted (for example metabolically or hydrolytically) into compounds according to the invention during their dwell time in the body.

In the context of the present invention, the substituents have the following meaning, unless specified otherwise:

Alkyl in the context of the invention represents a straight-chain or branched alkyl radical having the number of carbon atoms stated in each case. The following may be mentioned by way of example and by way of preference: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl, 2-ethylbutyl.

Cycloalkyl or carbocycle in the context of the invention represents a monocyclic saturated alkyl radical having the number of ring carbon atoms stated in each case. The following may be mentioned by way of example and by way of preference: cyclopropyl, cyclobutyl, cyclopentyl, cyclohexyl and cycloheptyl.

Alkenyl in the context of the invention represents a straight-chain or branched alkenyl radical having 2 to 6 carbon atoms and one or two double bonds. Preference is given to a straight-chain or branched alkenyl radical having 2 to 4 carbon atoms and one double bond. The following may be mentioned by way of example and by way of preference: vinyl, allyl, isopropenyl and n-but-2-en-1-yl.

Alkynyl in the context of the invention represents a straight-chain or branched alkynyl radical having 2 to 4 carbon atoms and one triple bond. The following may be mentioned by way of example and by way of preference: ethynyl, n-prop-1-yn-1-yl, n-prop-2-yn-1-yl, n-but-2-yn-1-yl and n-but-3-yn-1-yl.

Alkanediyl in the context of the invention represents a straight-chain or branched divalent alkyl radical having 1 to 4 carbon atoms. The following may be mentioned by way of example and by way of preference: methylene, 1,2-ethylene, ethane-1,1-diyl, 1,3-propylene, propane-1,1-diyl, propane-1,2-diyl, propane-2,2-diyl, 1,4-butylene, butane-1,2-diyl, butane-1,3-diyl and butane-2,3-diyl.

Alkoxy in the context of the invention represents a straight-chain or branched alkoxy radical having 1 to 4 carbon atoms. The following may be mentioned by way of example and by way of preference: methoxy, ethoxy, n-propoxy, isopropoxy, 1-methylpropoxy, n-butoxy, isobutoxy and tert-butoxy.

Alkylsulphonyl in the context of the invention represents a straight-chain or branched alkyl radical which has 1 to 4 carbon atoms and is attached via a sulphonyl group. The following may be mentioned by way of example and by way of preference: methylsulphonyl, ethylsulphonyl, n-propylsulphonyl, isopropylsulphonyl, n-butylsulphonyl and tert-butylsulphonyl.

A 4- to 7-membered heterocycle in the context of the invention represents a monocyclic saturated heterocycle which has a total of 4 to 7 ring atoms, which contains one or two ring heteroatoms from the group consisting of N, O, S, SO and $SO_2$ and which is attached via a ring carbon atom or, if appropriate, a ring nitrogen atom. The following may be mentioned by way of example: azetidinyl, oxetanyl, pyrrolidinyl, pyrazolidinyl, tetrahydrofuranyl, thiolanyl, piperidinyl, piperazinyl, tetrahydropyranyl, tetrahydrothiopyranyl, morpholinyl, thiomorpholinyl, hexahydroazepinyl and hexahydro-1,4-diazepinyl. Preference is given to azetidinyl, oxetanyl, pyrrolidinyl, tetrahydrofuranyl, piperidinyl, piperazinyl, tetrahydropyranyl and morpholinyl.

Heteroaryl in the context of the invention represents a monocyclic aromatic heterocycle (heteroaromatic) which has a total of 5 or 6 ring atoms, which contains up to three identical or different ring heteroatoms from the group consisting of N, O and S and is attached via a ring carbon atom or, if appropriate, a ring nitrogen atom. The following may be mentioned by way of example and by way of preference: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl and triazinyl.

Halogen in the context of the invention includes fluorine, chlorine, bromine and iodine. Preference is given to chlorine or fluorine.

In the formula of the group which may represent $R^3$ or $R^1$, the end point of the line marked by a * or # label does not represent a carbon atom or a $CH_2$ group but forms part of the bond to the atom which is designated in each case and to which $R^3$ and $R^1$, respectively, are attached.

If radicals in the compounds according to the invention are substituted, the radicals may, unless specified otherwise, be mono- or polysubstituted. In the context of the present invention, all radicals which occur more than once are defined independently of one another. Substitution by one, two or three identical or different substituents is preferred.

In the context of the present invention, the term "treatment" or "treat" includes the inhibition, delay, arrest, amelioration, attenuation, limitation, reduction, suppression, reversal or cure of a disease, a condition, a disorder, an injury and a health impairment, of the development, course or the progression of such states and/or the symptoms of such states. Here, the term "therapy" is understood to be synonymous with the term "treatment".

In the context of the present invention, the terms "prevention", "prophylaxis" or "precaution" are used synonymously and refer to the avoidance or reduction of the risk to get, to contract, to suffer from or to have a disease, a condition, a disorder, an injury or a health impairment, a development or a progression of such states and/or the symptoms of such states.

The treatment or the prevention of a disease, a condition, a disorder, an injury or a health impairment may take place partially or completely.

In the context of the present invention, preference is given to compounds of the formula (I) in which A represents $CH_2$, $R^1$ represents $(C_4-C_6)$-cycloalkyl or phenyl, where phenyl may be substituted by 1 to 3 substituents selected from the group consisting of fluorine and chlorine, $R^2$ represents methyl, ethyl or trifluoromethyl,
$R^3$ represents a group of the formula

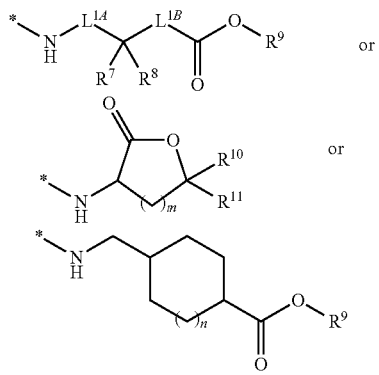

where
* represents the point of attachment to the carbonyl group,
$L^{1a}$ represents a bond or $(C_1-C_4)$-alkanediyl, where $(C_1-C_4)$-alkanediyl may be substituted by 1 to 3 substituents independently of one another selected from the group consisting of fluorine, trifluoromethyl, hydroxy and $(C_1-C_4)$-alkyl,
$L^{1B}$ represents a bond or $(C_1-C_4)$-alkanediyl,
where $(C_1-C_4)$-alkanediyl may be substituted by 1 to 3 substituents independently of one another selected from the group consisting of fluorine, trifluoromethyl, hydroxy and $(C_1-C_4)$-alkyl,
$R^7$ represents hydrogen, trifluoromethyl, $(C_1-C_6)$-alkyl, 5- or 6-membered heteroaryl or phenyl,
where $(C_1-C_6)$-alkyl may be substituted by 1 to 2 substituents independently of one another selected from the group consisting of fluorine, trifluoromethyl and phenyl,
where phenyl may be substituted by 1 or 2 substituents selected from the group consisting of fluorine and chlorine,
and
where phenyl and 5- or 6-membered heteroaryl may be substituted by 1 to 2 substituents independently of one another selected from the group consisting of fluorine, chlorine and cyano,
$R^8$ represents hydrogen, methyl or ethyl,
$R^9$ represents hydrogen, methyl or ethyl,
$R^{10}$ represents hydrogen or methyl,
$R^{11}$ represents hydrogen or methyl,
m represents 1, 2 or 3,
n represents 0, 1 or 2,
$R^4$ represents hydrogen,
$R^5$ represents hydrogen, fluorine, chlorine, difluoromethyl, trifluoromethyl, methyl or ethyl,
$R^6$ represents hydrogen,
and to N-oxides, salts, solvates, salts of the N-oxides and solvates of the N-oxides and salts thereof.

In the context of the present invention, particular preference is given to compounds of the formula (I) in which A represents $CH_2$,
$R^1$ represents a phenyl group of the formula

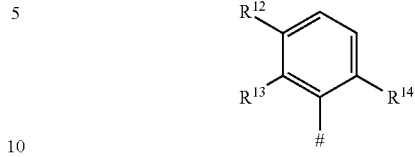

where
# represents the point of attachment to A,
and
$R^{12}$, $R^{13}$ and $R^{14}$ independently of one another represent hydrogen, fluorine or chlorine,
with the proviso that at least two of the radicals $R^{12}$, $R^{13}$, $R^{14}$ are different from hydrogen,
$R^2$ represents methyl,
$R^3$ represents a group of the formula

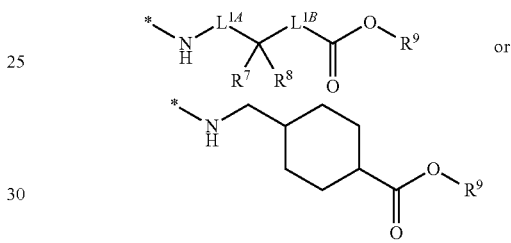

where
* represents the point of attachment to the carbonyl group,
$L^{1A}$ represents a bond or $(C_1-C_4)$-alkanediyl,
$L^{1B}$ represents a bond or $(C_1-C_4)$-alkanediyl,
$R^7$ represents hydrogen, trifluoromethyl, $(C_1-C_6)$-alkyl or phenyl,
where $(C_1-C_6)$-alkyl may be substituted by 1 to 2 substituents selected from the group consisting of fluorine and trifluoromethyl,
and
where phenyl may be substituted by 1 to 2 substituents selected from the group consisting of fluorine and chlorine,
$R^8$ represents hydrogen or methyl,
$R^9$ represents hydrogen, methyl or ethyl,
$R^4$ represents hydrogen,
$R^5$ represents hydrogen, fluorine, chlorine or methyl,
$R^6$ represents hydrogen,
and to N-oxides, salts, solvates, salts of the N-oxides and solvates of the N-oxides and salts thereof.

In the context of the present invention, preference is also given to compounds of the formula (I) in which
$R^1$ represents a phenyl group of the formula

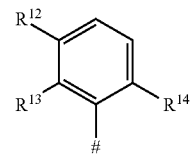

where
# represents the point of attachment to A,
and
$R^{12}$, $R^{13}$ and $R^{14}$ independently of one another represent hydrogen, fluorine or chlorine,
with the proviso that at least two of the radicals $R^{12}$, $R^{13}$, $R^{14}$ are different from hydrogen,
and to N-oxides, salts, solvates, salts of the N-oxides and solvates of the N-oxides and salts thereof.

In the context of the present invention, preference is also given to compounds of the formula (I) in which
$R^2$ represents methyl,
and to N-oxides, salts, solvates, salts of the N-oxides and solvates of the N-oxides and salts thereof.

In the context of the present invention, preference is also given to compounds of the formula (I) in which
$R^3$ represents a group of the formula

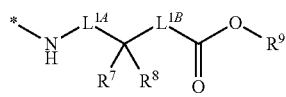

where
* represents the point of attachment to the carbonyl group,
$L^{1a}$ represents a bond,
and
$L^{1B}$ represents a bond,
and to N-oxides, salts, solvates, salts of the N-oxides and solvates of the N-oxides and salts thereof.

In the context of the present invention, preference is also given to compounds of the formula (I) in which
$R^3$ represents a group of the formula

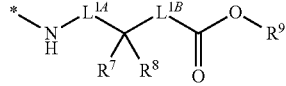

where
* represents the point of attachment to the carbonyl group,
$L^{1A}$ represents a bond,
and
$L^{1B}$ represents $(C_1-C_4)$-alkanediyl,
and to N-oxides, salts, solvates, salts of the N-oxides and solvates of the N-oxides and salts thereof.

In the context of the present invention, preference is also given to compounds of the formula (I) in which
$R^3$ represents a group of the formula

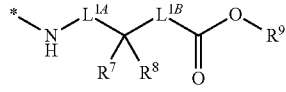

where
* represents the point of attachment to the carbonyl group,
$L^{1a}$ represents $(C_1-C_4)$-alkanediyl,
and
$L^{1B}$ represents $(C_1-C_4)$-alkanediyl,
and to N-oxides, salts, solvates, salts of the N-oxides and solvates of the N-oxides and salts thereof.

In the context of the present invention, preference is also given to compounds of the formula (I) in which
$R^3$ represents a group of the formula

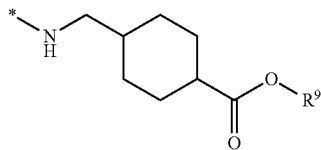

where
* represents the point of attachment to the carbonyl group,
and
$R^9$ represents methyl, ethyl or hydrogen,
and to N-oxides, salts, solvates, salts of the N-oxides and solvates of the N-oxides and salts thereof.

In the context of the present invention, preference is also given to compounds of the formula (I) in which
$R^4$ represents hydrogen,
and
$R^6$ represents hydrogen,
and to N-oxides, salts, solvates, salts of the N-oxides and solvates of the N-oxides and salts thereof.

In the context of the present invention, preference is also given to compounds of the formula (I) in which
$R^5$ represents hydrogen, fluorine, chlorine or methyl,
and to N-oxides, salts solvates, salts of the N-oxides and solvates of the N-oxides and salts thereof.

The definitions of radicals indicated specifically in the respective combinations or preferred combinations of radicals are replaced as desired irrespective of the particular combinations indicated for the radicals also by definitions of radicals of other combinations.

Combinations of two or more of the preferred ranges mentioned above are particularly preferred.

The invention furthermore provides a process for preparing the compounds of the formula (I) according to the invention, characterized in that

[A] a compound of the formula (II)

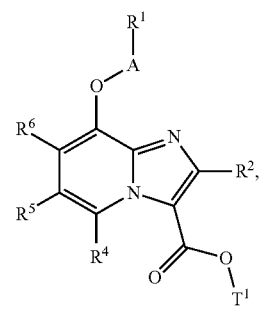

in which A, $R^1$, $R^2$, $R^4$, $R^5$ and $R^6$ each have the meanings given above and
$T^1$ represents $(C_1-C_4)$-alkyl or benzyl,
is reacted in an inert solvent in the presence of a suitable base or acid to give a carboxylic acid of the formula (III)

(III-A)

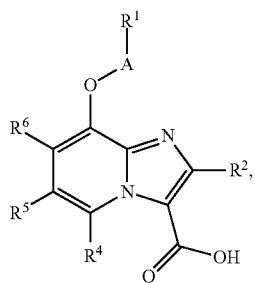

in which A, $R^1$, $R^2$, $R^4$, $R^5$ and $R^6$ each have the meanings given above,
and this is subsequently reacted in an inert solvent under amide coupling conditions with an amine of the formula (IV-A) or (IV-B)

(IV-A)

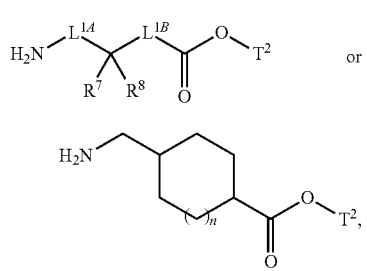

or (IV-B)

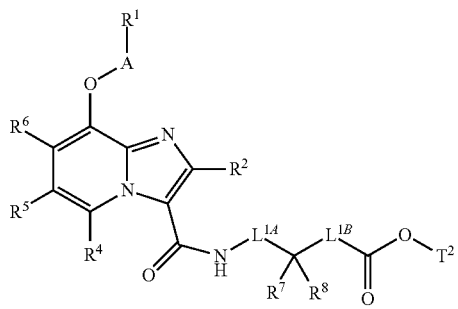

and the resulting compound of the formula (V-A) or (V-B)

(V-A)

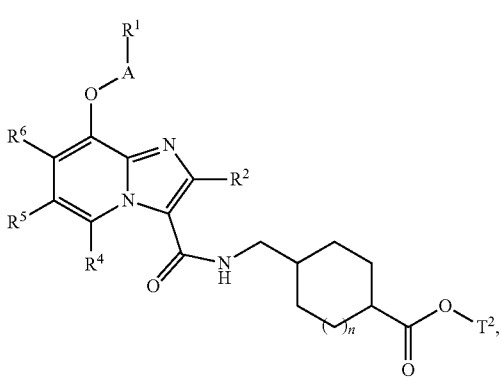

(V-B)

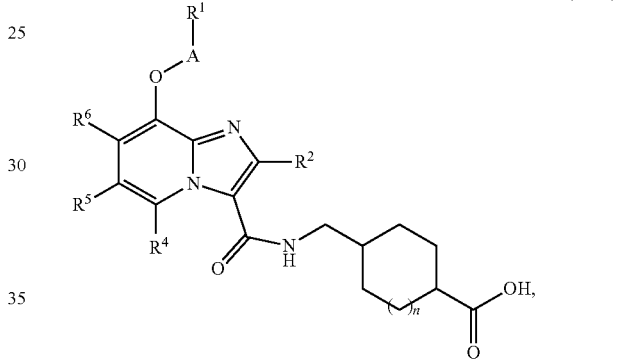

in which A, n, $R^1$, $R^2$, $R^4$, $R^5$, $R^6$, $L^{1A}$, $L^{1B}$, $R^7$ and $R^8$ each have the meanings given above and
$T^2$ represents $(C_1-C_6)$-alkyl,
is optionally reacted in an inert solvent in the presence of a suitable base or acid to give a carboxylic acid of the formula (VI-A) or (VI-B)

(VI-A)

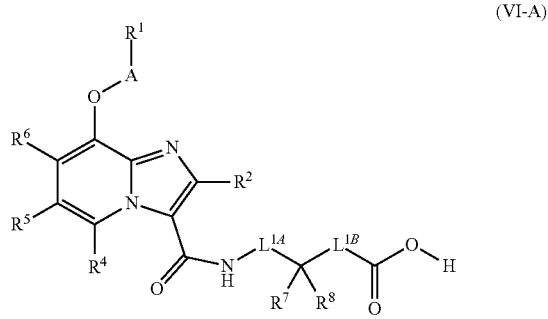

(VI-B)

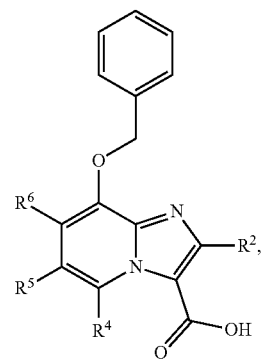

or
[B] a compound of the formula (III-B)

(III-B)

in which $R^2$, $R^4$, $R^5$ and $R^6$ each have the meanings given above,
is reacted in an inert solvent under amide coupling conditions with an amine of the formula (IV-A) or (IV-B) to give a compound of the formula (V-C) or (V-D),

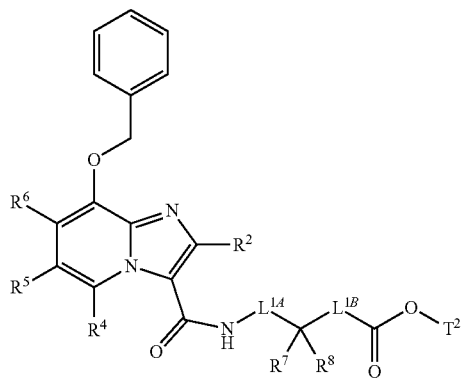

(V-C)

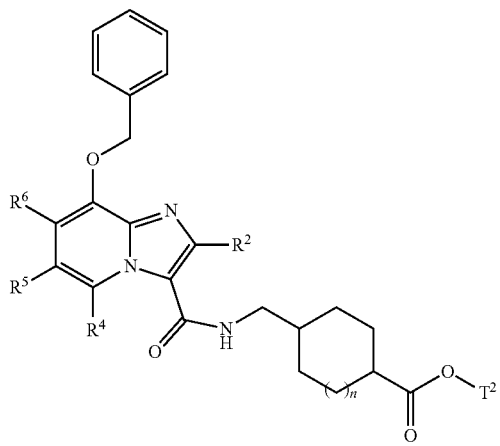

(V-D)

in which n, $R^2$, $R^4$, $R^5$, $R^6$, $L^{1A}$, $L^{1B}$, $R^7$ and $R^8$ each have the meanings given above, and
$T^2$ represents $(C_1-C_6)$-alkyl,
from this compound, the benzyl group is subsequently removed using methods known to the person skilled in the art and the resulting compounds of the formula (VII-A) or (VII-B)

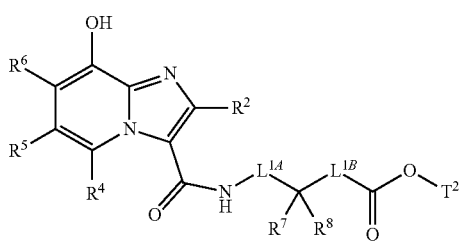

(VII-A)

(VII-B)

in which n, $R^2$, $R^4$, $R^5$, $R^6$, $L^{1A}$, $L^{1B}$, $R^7$ and $R^8$ each have the meanings given above, and $T^2$ represents $(C_1-C_6)$-alkyl,
is reacted in an inert solvent in the presence of a suitable base with a compound of the formula (VIII)

(VIII)

in which A and $R^1$ have the meanings given above and
X' represents a suitable leaving group, in particular chlorine, bromine, iodine, mesylate, triflate or tosylate,
and the compounds (V-A) or (V-B) resulting therefrom

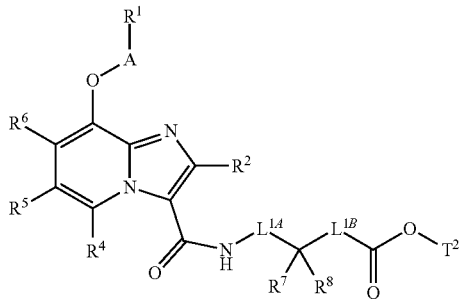

(V-A)

(V-B)

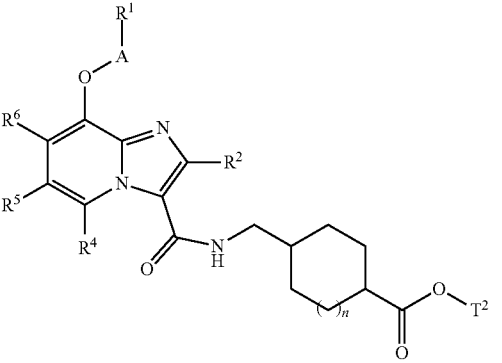

in which A, $R^1$, $R^2$, $R^4$, $R^5$, $R^6$, $L^{1A}$, $L^{1B}$, $R^7$ and $R^8$ each have the meanings given above, and
$T^2$ represents $(C_1-C_6)$-alkyl,
are optionally reacted in an inert solvent in the presence of a suitable base or acid to give a carboxylic acid of the formula (VI-A) or (VI-B)

(VI-A)

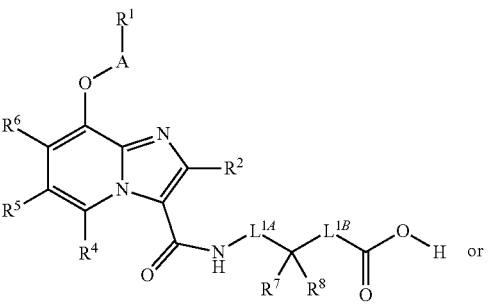

or (VI-B)

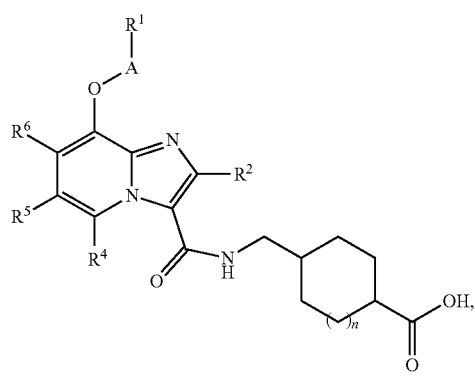

and the resulting compounds of the formula (I) are optionally converted with the appropriate (i) solvents and/or (ii) acids or bases into their solvates, salts and/or solvates of the salts.

The compounds of the formulae (V-A), (V-B), (V-C), (V-D), (VI-A) and (VI-B) form a subset of the compounds of the formula (I) according to the invention.

The preparation processes described can be illustrated in an exemplary manner by the synthesis scheme below (Scheme 1):

Scheme 1:

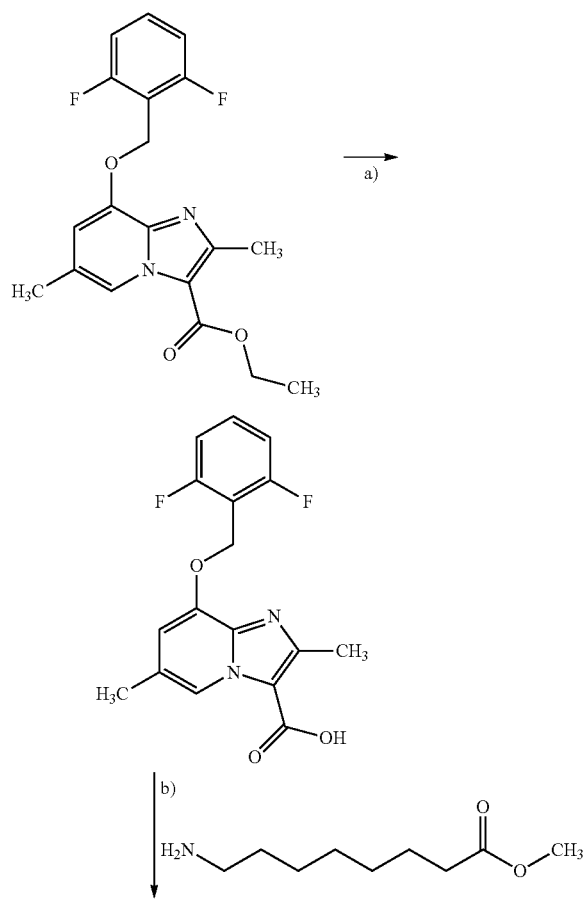

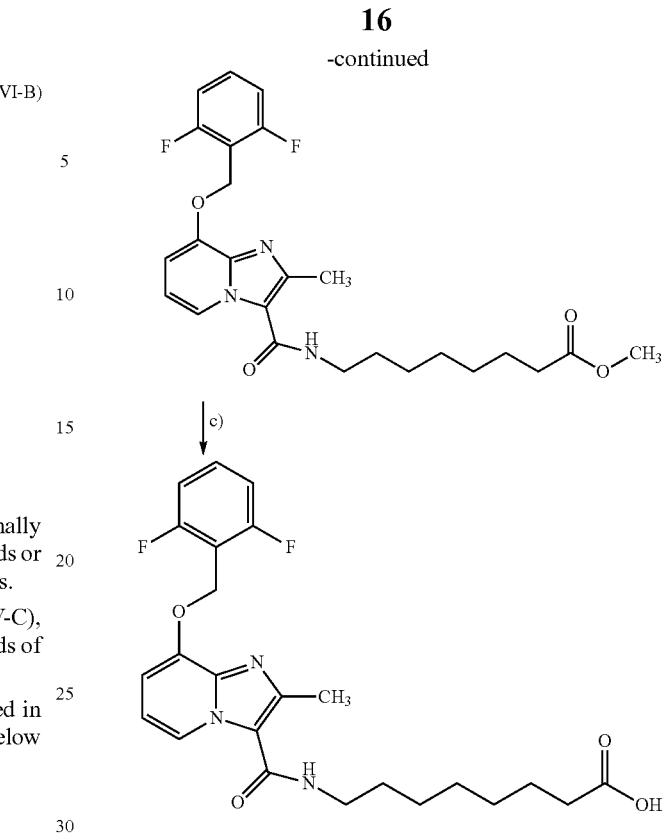

[a): lithium hydroxide, THF/methanol/H$_2$O, RT; b): TBTU, 4-methylmorpholine, DMF, RT; c): lithium hydroxide, THF/H$_2$O, RT].

The compounds of the formulae (VI) are commercially available, known from the literature or can be prepared analogously to processes known from the literature.

Inert solvents for the process steps (III-A)+(IV-A)→(V-A) and (III-A)+(IV-B)→(V-B) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methyl-pyrrolidone (NMP). It is also possible to use mixtures of the solvents mentioned. Preference is given to dichloromethane, tetrahydrofuran, dimethylformamide or mixtures of these solvents.

Suitable condensing agents for the amide formation in process steps (III-A)+(IV-A)→(V-A) and (III-A)+(IV-B)→ (V-B) are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethyl-carbodiimide hydrochloride (EDC), phosgene derivatives such as N,N'-carbonyldiimidazole (CDI), 1,2-oxazolium compounds such as 2-ethyl-5-phenyl-1,2-oxazolium 3-sulphate or 2-tert-butyl-5-methylisoxazolium perchlorate, acylamino compounds such as 2-ethoxy-1-ethoxycarbonyl-1,2-di-hydroquinoline, or isobutyl chloroformate, propanephosphonic anhydride (T3P), 1-chloro-N,N,2-trimethylprop1-ene-1-amine, diethyl cyanophosphonate, bis-(2-oxo-3-oxazolidinyl)phosphoryl chloride, benzotriazol-1-yloxytris(dimethylamino)phosphonium hexafluorophosphate, benzo-triazol-1- yloxytris(pyrrolidino)phosphonium hexafluorophosphate (PyBOP), O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyl-uronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), if appropriate in combination with further auxiliaries such as 1-hydroxy-benzotriazole (HOBt) or N-hydroxysuccinimide (HOSu), and also as bases alkali metal carbonates, for example sodium carbonate or potassium carbonate or sodium bicarbonate or potassium bicarbonate, or organic bases such as trialkylamines, for example triethylamine, N-methyl-morpholine, N-methylpiperidine or N,N-diisopropylethylamine. Preference is given to using TBTU in combination with N-methylmorpholine, HATU in combination with N,N-diisopropylethylamine or 1-chloro-N,N,2-trimethylprop-1-ene-lamine.

The condensations (III-A)+(IV-A)→(V-A) and (III-A)+(IV-B)→(V-B) are generally carried out in a temperature range of from −20° C. to +100° C., preferably at from 0° C. to +60° C. The reaction can be performed at atmospheric, elevated or at reduced pressure (for example from 0.5 to 5 bar). In general, the reaction is carried out at atmospheric pressure.

Alternatively, the carboxylic acids of the formula (III-A) can also initially be converted into the corresponding carbonyl chloride and this can then be reacted directly or in a separate reaction with an amine of the formula (IV-A) or (V-B) to give the compounds according to the invention. The formation of carbonyl chlorides from carboxylic acids is carried out by methods known to the person skilled in the art, for example by treatment with thionyl chloride, sulphuryl chloride or oxalyl chloride in the presence of a suitable base, for example in the presence of pyridine, and also optionally with addition of dimethylformamide, optionally in a suitable inert solvent.

The hydrolysis of the ester group $T^1$ of the compounds of the formula (II) is carried out by customary methods by treating the esters in inert solvents with acids or bases, where in the latter case the salts initially formed are converted into the free carboxylic acids by treatment with acid. In the case of the tert-butyl esters the ester cleavage is preferably carried out with acids. In the case of benzyl esters, the ester cleavage is preferably carried out hydrogenolytically using palladium on activated carbon or Raney nickel.

Suitable inert solvents for this reaction are water or the organic solvents customary for an ester cleavage. These preferably include alcohols such as methanol, ethanol, n-propanol, isopropanol, n-butanol, or tert-butanol, or ethers such as diethyl ether, tetrahydrofuran, 2-methyltetrahydrofuran, dioxane or glycol dimethyl ether, or other solvents such as acetone, dichloromethane, dimethyl-formamide or dimethyl sulphoxide. It is also possible to use mixtures of the solvents mentioned. In the case of a basic ester hydrolysis, preference is given to using mixtures of water with dioxane, tetrahydrofuran, methanol and/or ethanol.

Suitable bases for the ester hydrolysis are the customary inorganic bases. These preferably include alkali metal or alkaline earth metal hydroxides, for example sodium hydroxide, lithium hydroxide, potassium hydroxide or barium hydroxide, or alkali metal or alkaline earth metal carbonates such as sodium carbonate, potassium carbonate or calcium carbonate. Particular preference is given to sodium hydroxide or lithium hydroxide.

Suitable acids for the ester cleavage are, in general, sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluoromethanesulphonic acid, or mixtures thereof, if appropriate with addition of water. Preference is given to hydrogen chloride or trifluoroacetic acid in the case of the tert-butyl esters and hydrochloric acid in the case of the methyl esters.

The ester cleavage is generally carried out in a temperature range of from 0° C. to +100° C., preferably at from +0° C. to +50° C.

The reactions mentioned can be carried out at atmospheric, elevated or reduced pressure (for example from 0.5 to 5 bar). In general, the reactions are in each case carried out at atmospheric pressure.

Inert solvents for the process step (VII-A)+(VIII)→(V-A) and (VII-B)+(VIII)→(V-B) are, for example, halogenated hydrocarbons such as dichloromethane, trichloromethane, carbon tetrachloride, trichloroethylene or chlorobenzene, ethers such as diethyl ether, dioxane, tetrahydro-furan, glycol dimethyl ether or diethylene glycol dimethyl ether, hydrocarbons such as benzene, toluene, xylene, hexane, cyclohexane or mineral oil fractions, or other solvents such as acetone, methyl ethyl ketone, ethyl acetate, acetonitrile, N,N-dimethylformamide, N,N-dimethylacetamide, dimethyl sulphoxide, N,N'-dimethylpropyleneurea (DMPU), N-methylpyrrolidone (NMP) or pyridine. It is also possible to use mixtures of the solvents mentioned. Preference is given to using dimethylformamide or dimethyl sulphoxide.

Suitable bases for the process step (VII-A)+(VIII)→(V-A) and (VII-B)+(VIII)→(V-B) are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, if appropriate with addition of an alkali metal iodide, for example sodium iodide or potassium iodide, alkali alkoxides such as sodium methoxide or potassium methoxide, sodium ethoxide or potassium ethoxide or sodium tert-butoxide or potassium tert-butoxide, alkali metal hydrides such as sodium hydride or potassium hydride, amides such as sodium amide, lithium bis(trimethylsilyl)amide or potassium bis(trimethylsilyl)amide or lithium diisopropylamide, or organic amines such as triethylamine, N-methylmorpholine, N-methyl-piperidine, N,N-diisopropylethylamine, pyridine, 4-(N,N-dimethylamino)pyridine (DMAP), 1,5-diazabicyclo[4.3.0]non-5-ene (DBN), 1,8-diazabicyclo[5.4.0]undec-7-ene (DBU) or 1,4-diazabicyclo[2.2.2]octane)(DABCO®). Preference is given to using potassium carbonate, caesium carbonate or sodium methoxide.

The reaction is generally carried out in a temperature range of from 0° C. to +120° C., preferably at from +20° C. to +80° C., if appropriate in a microwave. The reaction can be carried out at atmospheric, elevated or reduced pressure (for example from 0.5 to 5 bar).

In the process steps described above, any functional groups present—such as, in particular amino, hydroxyl and carboxyl groups—may, if expedient or required, also be present in protected form. Here, the introduction and removal of such protective groups is carried out by customary methods [see, for example, T. W. Greene and P. G. M. Wuts, *Protective Groups in Organic Synthesis*, Wiley, New York, 1999; M. Bodanszky and A. Bodanszky, *The Practice of Peptide Synthesis*, Springer-Verlag, Berlin, 1984]. If a plurality of protected groups is present, their release may, if appropriate, take place simultaneously in a one-pot reaction or else in separate reaction steps.

Preferred for use as amino protective group is tert-butoxycarbonyl (Boc) or benzyloxycarbonyl (Z). As protective group for a hydroxyl or carboxyl function, preference is given to using tert-butyl or benzyl. The removal of these protective groups is carried out by customary methods, preferably by reaction with a strong acid such as hydrogen chloride, hydrogen bromide or trifluoroacetic acid in an inert solvent such as dioxane, diethyl ether, dichloromethane or acetic acid; if appropriate, the removal can also be carried out without any additional inert solvent. In the case of benzyl and benzyloxycarbonyl as protective group, these can also be removed by hydrogenolysis in the presence of a palladium catalyst. If appropriate, the removal of the protective groups mentioned can be performed simultaneously in a one-pot reaction or in separate reaction steps.

Here, the removal of the benzyl group in reaction step (V-A)→(VII-A), (V-B)→(VII-B) is carried out by customary methods known from protective group chemistry, preferably by hydrogenolysis in the presence of a palladium catalyst such as palladium on activated carbon in an inert solvent, for example ethanol or ethyl acetate [see also, for example, T. W. Greene and P. G. M. Wuts, *Protective Groups in Organic Synthesis*, Wiley, New York, 1999].

The compounds of the formula (II) are known from the literature or can be prepared by reacting a compound of the formula (IX)

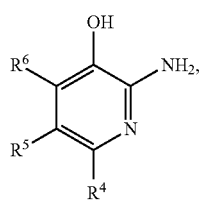

in which $R^4$, $R^5$ and $R^6$ have the meanings given above, in an inert solvent in the presence of a suitable base with a compound of the formula (VIII) to give a compound of the formula (VIII)

in which A and $R^1$ have the meanings given above, and $X^1$ is a suitable leaving group, in particular chlorine, bromine, iodine, mesylate, triflate or tosylate, to give a compound of the formula (X)

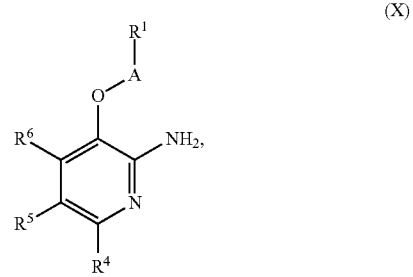

in which A, $R^1$, $R^4$, $R^5$ and $R^6$ each have the meanings given above, and this is then reacted in an inert solvent with a compound of the formula (XI)

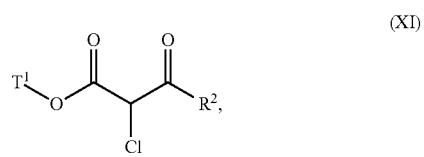

in which $R^2$ and $T^1$ each have the meanings given above.

The process described is illustrated in an exemplary manner by the scheme below (Scheme 2):

Scheme 2:

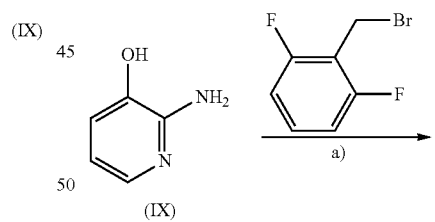

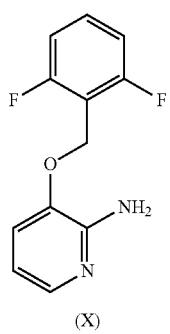

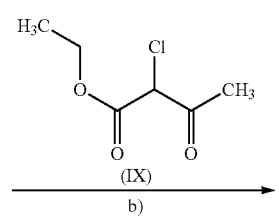

-continued

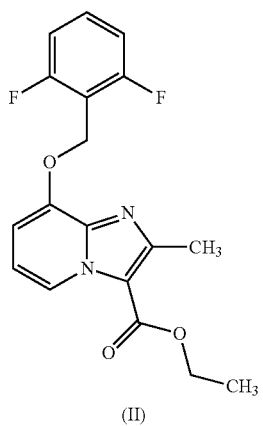

(II)

[a): i) NaOMe, MeOH, RT; ii) DMSO, RT; b): EtOH, molecular sieve, reflux].

Inert solvents for the ring closure affording the imidazo[1,2-a]pyridine skeleton (IX)+(XI)→(II) are the customary organic solvents. These preferably include alcohols such as methanol, ethanol, n-propanol, isopropanol, n-butanol, n-pentanol or tert-butanol, or ethers such as diethyl ether, tetra-hydrofuran, 2-methyltetrahydrofuran, dioxane or glycol dimethyl ether, or other solvents such as acetone, dichloromethane, 1,2-dichloroethane, acetonitrile, dimethylformamide or dimethyl-sulphoxide. It is also possible to use mixtures of the solvents mentioned. Preference is given to using ethanol.

The ring closure is usually carried out in a temperature range from +50° C. to +150° C., preferably at from +50° C. to +100° C., if appropriate in a microwave oven.

The ring closure (IX)+(X)→(III) is optionally carried out in the presence of dehydrating agents, for example in the presence of molecular sieve (pore size 4 Å) or using a water separator. The reaction (IX)+(X)→(II) is carried out using an excess of the reagent of the formula (IX), for example using 1 to 20 equivalents of reagent (IX), if appropriate with addition of bases (such as sodium bicarbonate), where the addition of this reagent can be carried out once or in several portions.

Alternatively to the introductions of R' shown in Scheme 2 by reaction of the compounds (VII-A) or (IX) with compounds of the formula (VIII), it is also possible—as shown in Scheme 3—to react these intermediates with alcohols of the formula (XII) under the conditions of the Mitsunobu reaction.

Scheme 3:

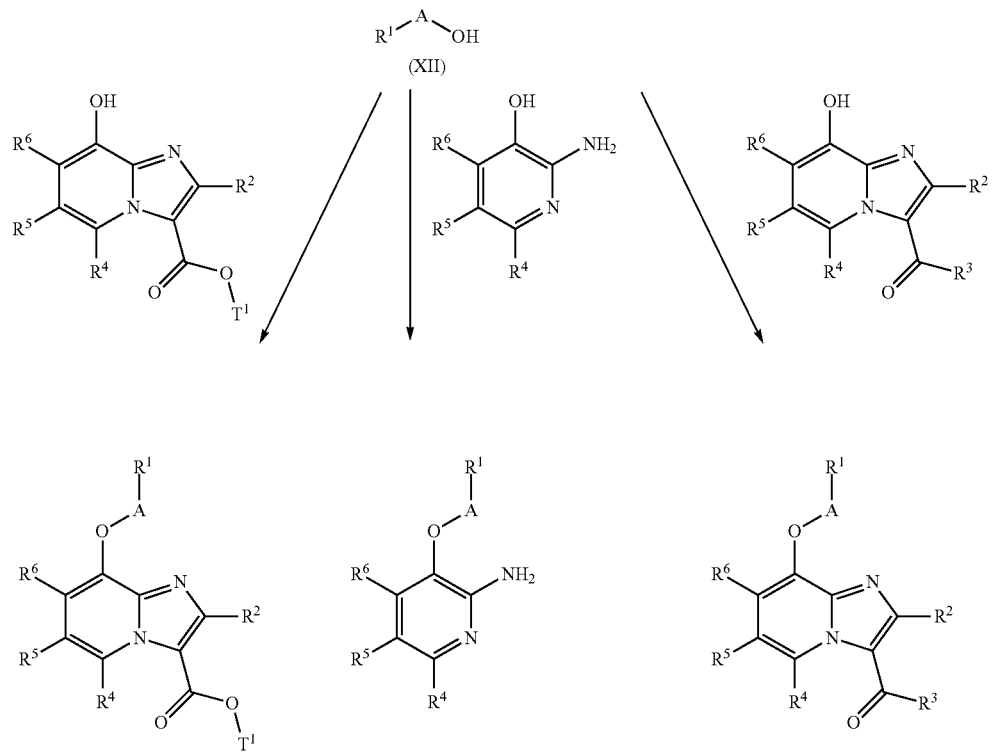

Typical reaction conditions for such Mitsunobu condensations of phenols with alcohols can be found in the relevant literature, for example Hughes, D. L. *Org. React.* 1992, 42, 335; Dembinski, R. *Eur. J. Org. Chem.* 2004, 2763. Typically, the compound is reacted with an activating agent, for example diethyl azodicarboxylate (DEAD) or diisopropyl azodicarboxylate (DIAD), and a phosphine reagent, for example triphenylphosphine or tributylphosphine, in an inert solvent, for example THF, dichloromethane, toluene or DMF, at a temperature between 0° C. and the boiling point of the solvent employed.

Further compounds according to the invention can optionally also be prepared by converting functional groups of individual substituents, in particular those listed under $R^3$, starting with the compounds of the formula (I) obtained by the above processes. These conversions are carried out by customary methods known to the person skilled in the art and include, for example, reactions such as nucleophilic and electrophilic substitutions, oxidations, reductions, hydrogenations, transition metal-catalyzed coupling reactions, eliminations, alkylation, amination, esterification, ester cleavage, etherification, ether cleavage, formation of carboxamides, and also the introduction and removal of temporary protective groups.

The compounds according to the invention have useful pharmacological properties and can be employed for the prevention and treatment of disorders in humans and animals. The compounds according to the invention open up a further treatment alternative and are therefore an enrichment of pharmacy.

The compounds according to the invention bring about vessel relaxation and inhibition of thrombocyte aggregation and lead to a lowering of blood pressure and to an increase in coronary blood flow. These effects are due to direct stimulation of soluble guanylate cyclase and an increase in intracellular cGMP. Moreover, the compounds according to the invention intensify the action of substances that raise the cGMP level, for example EDRF (endothelium-derived relaxing factor), NO donors, protoporphyrin IX, arachidonic acid or phenylhydrazine derivatives.

The compounds according to the invention are suitable for the treatment and/or prophylaxis of cardiovascular, pulmonary, thromboembolic and fibrotic diseases.

The compounds according to the invention can therefore be used in medicinal products for the treatment and/or prophylaxis of cardiovascular diseases, for example high blood pressure (hypertension), resistant hypertension, acute and chronic heart failure, coronary heart disease, stable and unstable angina pectoris, peripheral and cardiac vascular diseases, arrhythmias, disturbances of atrial and ventricular rhythm and conduction disturbances, for example atrioventricular blocks of degree I-III (AVB I-III), supraventricular tachyarrhythmia, atrial fibrillation, atrial flutter, ventricular fibrillation, ventricular flutter, ventricular tachyarrhythmia, torsade-de-pointes tachycardia, atrial and ventricular extrasystoles, AV-junction extrasystoles, sick-sinus syndrome, syncopes, AV-node reentry tachycardia, Wolff-Parkinson-White syndrome, acute coronary syndrome (ACS), autoimmune heart diseases (pericarditis, endocarditis, valvulitis, aortitis, cardiomyopathies), shock such as cardiogenic shock, septic shock and anaphylactic shock, aneurysms, Boxer cardiomyopathy (premature ventricular contraction (PVC)), for the treatment and/or prophylaxis of thromboembolic diseases and ischaemias such as myocardial ischaemia, myocardial infarction, stroke, cardiac hypertrophy, transient ischaemic attacks, preeclampsia, inflammatory cardiovascular diseases, spasms of the coronary arteries and peripheral arteries, development of oedema, for example pulmonary oedema, cerebral oedema, renal oedema or oedema due to heart failure, peripheral perfusion disturbances, reperfusion injury, arterial and venous thromboses, microalbuminuria, myocardial insufficiency, endothelial dysfunction, for preventing restenoses such as after thrombolysis therapies, percutaneous transluminal angioplasty (PTA), transluminal coronary angioplasty (PTCA), heart transplant and bypass operations, and micro- and macrovascular damage (vasculitis), increased level of fibrinogen and of low-density LDL and increased concentrations of plasminogen activator inhibitor 1 (PAI-1), and for the treatment and/or prophylaxis of erectile dysfunction and female sexual dysfunction.

In the sense of the present invention, the term heart failure comprises both acute and chronic manifestations of heart failure, as well as more specific or related forms of disease such as acute decompensated heart failure, right ventricular failure, left ventricular failure, total heart failure, ischaemic cardiomyopathy, dilatated cardiomyopathy, hypertrophic cardiomyopathy, idiopathic cardiomyopathy, congenital heart defects, heart failure with valvular defects, mitral valve stenosis, mitral valve insufficiency, aortic valve stenosis, aortic valve insufficiency, tricuspid stenosis, tricuspid insufficiency, pulmonary valve stenosis, pulmonary valve insufficiency, combined valvular defects, heart muscle inflammation (myocarditis), chronic myocarditis, acute myocarditis, viral myocarditis, diabetic heart failure, alcoholic cardiomyopathy, storage cardiomyopathies, diastolic heart failure and also systolic heart failure and acute phases of an existing chronic heart failure (worsening heart failure).

In addition, the compounds according to the invention can also be used for the treatment and/or prophylaxis of arteriosclerosis, disturbances of lipid metabolism, hypolipoproteinaemias, dyslipidaemias, hypertriglyceridaemias, hyperlipidaemias, hypercholesterolaemias, abetalipoproteinaemia, sitosterolaemia, xanthomatosis, Tangier disease, adiposity, obesity, and combined hyperlipidaemias and metabolic syndrome.

Moreover, the compounds according to the invention can be used for the treatment and/or prophylaxis of primary and secondary Raynaud phenomenon, microcirculation disturbances, claudication, peripheral and autonomic neuropathies, diabetic microangiopathies, diabetic retinopathy, diabetic limb ulcers, gangrene, CREST syndrome, erythematous disorders, onychomycosis, rheumatic diseases and for promoting wound healing.

Furthermore, the compounds according to the invention are suitable for treating urological diseases, for example benign prostatic syndrome (BPS), benign prostatic hyperplasia (BPH), benign prostatic enlargement (BPE), bladder outlet obstruction (BOO), lower urinary tract syndromes (LUTS, including feline urological syndrome (FUS)), diseases of the urogenital system including neurogenic overactive bladder (OAB) and (IC), urinary incontinence (UI) for example mixed, urge, stress, or overflow incontinence (MUI, UUI, SUI, OUI), pelvic pains, benign and malignant diseases of the organs of the male and female urogenital system.

Furthermore, the compounds according to the invention are suitable for the treatment and/or prophylaxis of kidney diseases, in particular acute and chronic renal insufficiency, and acute and chronic renal failure. In the sense of the present invention, the term renal insufficiency comprises both acute and chronic manifestations of renal insufficiency, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney transplant rejection, immune complex-induced kidney diseases, nephropathy induced by toxic substances, contrast medium-induced nephropathy, diabetic and non-diabetic nephropathy, pyelonephritis, renal cysts, nephrosclerosis, hypertensive nephrosclerosis and nephrotic syndrome, which can be characterized diagnostically for example by abnormally reduced creatinine and/or water excretion, abnormally increased blood concentrations of urea, nitrogen, potassium and/or creatinine, altered activity of renal enzymes such as e.g. glutamyl synthetase, altered urine osmolarity or urine volume, increased microalbuminuria, macroalbuminuria, lesions of glomeruli and arterioles, tubular dilatation, hyperphosphataemia and/or need for dialysis. The present invention also comprises the use of the compounds according to the invention for the treatment and/or prophylaxis of sequelae of renal insufficiency, for example pulmonary oedema, heart failure, uraemia, anaemia, electrolyte disturbances (e.g. hyperkalaemia, hyponatraemia) and disturbances in bone and carbohydrate metabolism.

Furthermore, the compounds according to the invention are also suitable for the treatment and/or prophylaxis of asthmatic diseases, pulmonary arterial hypertension (PAH) and other forms of pulmonary hypertension (PH), comprising pulmonary hypertension associated with left ventricular disease, HIV, sickle cell anaemia, thromboembolism (CTEPH), sarcoidosis, COPD or pulmonary fibrosis, chronic obstructive pulmonary disease (COPD), acute respiratory distress syndrome (ARDS), acute lung injury (ALI), alpha-1-antitrypsin deficiency (AATD), pulmonary fibrosis, pulmonary emphysema (e.g. smoking-induced pulmonary emphysema) and cystic fibrosis (CF).

The compounds described in the present invention are also active substances for controlling diseases in the central nervous system that are characterized by disturbances of the NO/cGMP system. In particular, they are suitable for improving perception, capacity for concentration, capacity for learning or memory performance after cognitive disturbances, such as occur in particular in situations/diseases/syndromes such as mild cognitive impairment, age-related learning and memory disturbances, age-related memory loss, vascular dementia, head injury, stroke, post-stroke dementia, post-traumatic head injury, general disturbances of concentration, disturbances of concentration in children with learning and memory problems, Alzheimer's disease, Lewy body dementia, dementia with frontal lobe degeneration including Pick's syndrome, Parkinson's disease, progressive nuclear palsy, dementia with corticobasal degeneration, amyotrophic lateral sclerosis (ALS), Huntington's disease, demyelination, multiple sclerosis, thalamic degeneration, Creutzfeldt-Jakob dementia, HIV-dementia, schizophrenia with dementia or Korsakoff psychosis. They are also suitable for the treatment and/or prophylaxis of diseases of the central nervous system such as anxiety, tension and depression, CNS-related sexual dysfunctions and sleep disturbances and for controlling pathological eating disorders and use of luxury foods and addictive drugs.

Furthermore, the compounds according to the invention are also suitable for controlling cerebral perfusion and are effective agents for combating migraines. They are also suitable for the prophylaxis and control of consequences of cerebral infarctions (apoplexia cerebri) such as stroke, cerebral ischaemias and head injury. The compounds according to the invention can also be used for controlling pain states and tinnitus.

In addition, the compounds according to the invention possess anti-inflammatory action and can therefore be used as anti-inflammatory agents for the treatment and/or prophylaxis of sepsis (SIRS), multiple organ failure (MODS, MOF), inflammatory diseases of the kidney, chronic intestinal inflammations (IBD, Crohn's disease, UC), pancreatitis, peritonitis, rheumatoid diseases, inflammatory skin diseases and inflammatory eye diseases.

Moreover, the compounds according to the invention can also be used for the treatment and/or prophylaxis of autoimmune diseases.

Furthermore, the compounds according to the invention are suitable for the treatment and/or prophylaxis of fibrotic diseases of the internal organs, for example of the lung, heart, kidney, bone marrow and in particular of the liver, and dermatological fibroses and fibrotic diseases of the eye. In the sense of the present invention, the term fibrotic diseases comprises in particular the following terms: hepatic fibrosis, hepatic cirrhosis, pulmonary fibrosis, endomyocardial fibrosis, nephropathy, glomerulonephritis, interstitial renal fibrosis, fibrotic lesions as a consequence of diabetes, bone marrow fibrosis and similar fibrotic diseases, scleroderma, morphea, keloids, hypertrophic scars (including after surgery), naevi, diabetic retinopathy, proliferative vitreoretinopathy and connective tissue diseases (e.g. sarcoidosis).

Furthermore, the compounds according to the invention are suitable for controlling postoperative scarring, e.g. as a result of glaucoma operations.

The compounds according to the invention can also be used cosmetically for ageing and keratinizing skin.

Moreover, the compounds according to the invention are suitable for the treatment and/or prophylaxis of hepatitis, neoplasms, osteoporosis, glaucoma and gastroparesis.

The present invention further relates to the use of the compounds according to the invention for the treatment and/or prophylaxis of diseases, in particular the aforementioned diseases.

The present invention further relates to the use of the compounds according to the invention for the treatment and/or prophylaxis of heart failure, angina pectoris, hypertension, pulmonary hypertension, ischaemias, vascular diseases, renal insufficiency, thromboembolic diseases, fibrotic diseases and arteriosclerosis.

The present invention further relates to the compounds according to the invention for use in a method for the treatment and/or prophylaxis of heart failure, angina pectoris, hypertension, pulmonary hypertension, ischaemias, vascular diseases, renal insufficiency, thromboembolic diseases, fibrotic diseases and arteriosclerosis.

The present invention further relates to the use of the compounds according to the invention for producing a medicinal product for the treatment and/or prophylaxis of diseases, in particular the aforementioned diseases.

The present invention further relates to the use of the compounds according to the invention for producing a medicinal product for the treatment and/or prophylaxis of heart failure, angina pectoris, hypertension, pulmonary hypertension, ischaemias, vascular diseases, renal insufficiency, thromboembolic diseases, fibrotic diseases and arteriosclerosis.

The present invention further relates to a method for the treatment and/or prophylaxis of diseases, in particular the aforementioned diseases, using an effective amount of at least one of the compounds according to the invention.

The present invention further relates to a method for the treatment and/or prophylaxis of heart failure, angina pectoris, hypertension, pulmonary hypertension, ischaemias, vascular diseases, renal insufficiency, thromboembolic diseases, fibrotic diseases and arteriosclerosis, using an effective amount of at least one of the compounds according to the invention.

The compounds according to the invention can be used alone or in combination with other active substances if necessary. The present invention further relates to medicinal products containing at least one of the compounds according to the invention and one or more further active substances, in particular for the treatment and/or prophylaxis of the aforementioned diseases. As suitable combination active substances, we may mention for example and preferably:

organic nitrates and NO-donors, for example sodium nitroprusside, nitroglycerin, isosorbide mononitrate, isosorbide dinitrate, molsidomine or SIN-1, and inhalational NO;

compounds that inhibit the degradation of cyclic guanosine monophosphate (cGMP), for example inhibitors of phosphodiesterases (PDE) 1, 2 and/or 5, in particular PDE-5 inhibitors such as sildenafil, vardenafil and tadalafil;

antithrombotic agents, for example and preferably from the group of platelet aggregation inhibitors, anticoagulants or profibrinolytic substances;

active substances for lowering blood pressure, for example and preferably from the group of calcium antagonists, angiotensin AII antagonists, ACE inhibitors, endothelin antagonists, renin inhibitors, alpha-blockers, beta-blockers, mineralocorticoid receptor antagonists and diuretics; and/or active substances that alter fat metabolism, for example and preferably from the group of thyroid receptor agonists, cholesterol synthesis inhibitors such as for example and preferably HMG-CoA-reductase or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists.

Antithrombotic agents are preferably to be understood as compounds from the group of platelet aggregation inhibitors, anticoagulants or profibrinolytic substances.

In a preferred embodiment of the invention, the compounds according to the invention are administered in combination with a platelet aggregation inhibitor, for example and preferably aspirin, clopidogrel, ticlopidine or dipyridamole.

In a preferred embodiment of the invention, the compounds according to the invention are administered in combination with a thrombin inhibitor, for example and preferably ximelagatran, dabigatran, melagatran, bivalirudin or Clexane.

In a preferred embodiment of the invention, the compounds according to the invention are administered in combination with a GPIIb/IIIa antagonist, for example and preferably tirofiban or abciximab.

In a preferred embodiment of the invention, the compounds according to the invention are administered in combination with a factor Xa inhibitor, for example and preferably rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, for example and preferably coumarin.

The agents for lowering blood pressure are preferably to be understood as compounds from the group of calcium antagonists, angiotensin AII antagonists, ACE inhibitors, endothelin antagonists, renin inhibitors, alpha-blockers, beta-blockers, mineralocorticoid-receptor antagonists and diuretics.

In a preferred embodiment of the invention, the compounds according to the invention are administered in combination with a calcium antagonist, for example and preferably nifedipine, amlodipine, verapamil or diltiazem.

In a preferred embodiment of the invention, the compounds according to the invention are administered in combination with an alpha-1-receptor blocker, for example and preferably prazosin.

In a preferred embodiment of the invention, the compounds according to the invention are administered in combination with a beta-blocker, for example and preferably propranolol, atenolol, timolol, pindolol, alprenolol, oxprenolol, penbutolol, bupranolol, metipranolol, nadolol, mepindolol, carazolol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, for example and preferably losartan, candesartan, valsartan, telmisartan or embursatan.

In a preferred embodiment of the invention, the compounds according to the invention are administered in combination with an ACE inhibitor, for example and preferably enalapril, captopril, lisinopril, ramipril, delapril, fosinopril, quinopril, perindopril or trandopril.

In a preferred embodiment of the invention, the compounds according to the invention are administered in combination with an endothelin antagonist, for example and preferably bosentan, darusentan, ambrisentan or sitaxsentan.

In a preferred embodiment of the invention, the compounds according to the invention are administered in combination with a renin inhibitor, for example and preferably aliskiren, SPP-600 or SPP-800.

In a preferred embodiment of the invention, the compounds according to the invention are administered in combination with a mineralocorticoid-receptor antagonist, for example and preferably spironolactone or eplerenone.

In a preferred embodiment of the invention, the compounds according to the invention are administered in combination with a loop diuretic, for example furosemide, torasemide, bumetanide and piretanide, with potassium-sparing diuretics for example amiloride and triamterene, with aldosterone antagonists, for example spironolactone, potassium canrenoate and eplerenone and thiazide diuretics, for example hydrochlorothiazide, chlorthalidone, xipamide, and indapamide.

Agents altering fat metabolism are preferably to be understood as compounds from the group of CETP inhibitors, thyroid receptor agonists, cholesterol synthesis inhibitors such as HMG-CoA-reductase or squalene synthesis inhibitors, the ACAT inhibitors, MTP inhibitors, PPAR-alpha, PPAR-gamma and/or PPAR-delta agonists, cholesterol-absorption inhibitors, polymeric bile acid adsorbers, bile acid reabsorption inhibitors, lipase inhibitors and the lipoprotein (a) antagonists.

In a preferred embodiment of the invention, the compounds according to the invention are administered in combination with a CETP inhibitor, for example and preferably dalcetrapib, BAY 60-5521, anacetrapib or CETP-vaccine (CETi-1).

In a preferred embodiment of the invention, the compounds according to the invention are administered in combination with a thyroid receptor agonist, for example and preferably D-thyroxin, 3,5,3'-triiodothyronin (T3), CGS 23425 or axitirome (CGS 26214).

In a preferred embodiment of the invention, the compounds according to the invention are administered in combination with an HMG-CoA-reductase inhibitor from the class of statins, for example and preferably lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, for example and preferably BMS-188494 or TAK-475.

In a preferred embodiment of the invention, the compounds according to the invention are administered in combination with an ACAT inhibitor, for example and preferably avasimibe, melinamide, pactimibe, eflucimibe or SMP-797.

In a preferred embodiment of the invention, the compounds according to the invention are administered in combination with an MTP inhibitor, for example and preferably implitapide, BMS-201038, R-103757 or JTT-130.

In a preferred embodiment of the invention, the compounds according to the invention are administered in combination with a PPAR-gamma agonist, for example and preferably pioglitazone or rosiglitazone.

In a preferred embodiment of the invention, the compounds according to the invention are administered in combination with a PPAR-delta agonist, for example and preferably GW 501516 or BAY 68-5042.

In a preferred embodiment of the invention, the compounds according to the invention are administered in combination with a cholesterol-absorption inhibitor, for example and preferably ezetimibe, tiqueside or pamaqueside.

In a preferred embodiment of the invention, the compounds according to the invention are administered in combination with a lipase inhibitor, for example and preferably orlistat.

In a preferred embodiment of the invention, the compounds according to the invention are administered in combination with a polymeric bile acid adsorber, for example and preferably cholestyramine, colestipol, colesolvam, CholestaGel or colestimide.

In a preferred embodiment of the invention, the compounds according to the invention are administered in combination with a bile acid reabsorption inhibitor, for example and preferably ASBT (=IBAT) inhibitors, e.g. AZD-7806, S-8921, AK-105, BARI-1741, SC-435 or SC-635.

In a preferred embodiment of the invention, the compounds according to the invention are administered in combination with a lipoprotein(a) antagonist, for example and preferably gemcabene calcium (CI-1027) or nicotinic acid.

The present invention further relates to medicinal products that contain at least one compound according to the invention, usually together with one or more inert, non-toxic, pharmaceutically suitable excipients, and use thereof for the aforementioned purposes.

The compounds according to the invention can have systemic and/or local action. For this purpose they can be applied in a suitable way, e.g. by oral, parenteral, pulmonary, nasal, sublingual, lingual, buccal, rectal, dermal, transdermal, conjunctival, or otic administration or as implant or stent.

For these routes of application, the compounds according to the invention can be administered in suitable dosage forms.

Dosage forms functioning according to the prior art, for rapid and/or modified release of the compounds according to the invention, which contain the compounds according to the invention in crystalline and/or amorphized and/or dissolved form, e.g. tablets (uncoated or coated tablets, for example with enteric coatings or coatings with delayed dissolution or insoluble coatings, which control the release of the compound according to the invention), tablets or films/wafers that disintegrate rapidly in the oral cavity, films/lyophilizates, capsules (for example hard or soft gelatin capsules), sugar-coated pills, granules, pellets, powders, emulsions, suspensions, aerosols or solutions, are suitable for oral administration.

Parenteral administration can take place avoiding an absorption step (e.g. intravenous, intraarterial, intracardiac, intraspinal or intralumbar) or including absorption (e.g. intramuscular, subcutaneous, intracutaneous, percutaneous or intraperitoneal). Injection and infusion preparations in the form of solutions, suspensions, emulsions, lyophilizates or sterile powders are suitable, among others, as dosage forms for parenteral application.

Inhaled pharmaceutical forms (including powder inhalers, nebulizers), nasal drops, solutions or sprays, tablets, films/wafers or capsules for lingual, sublingual or buccal application, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, dusting powders, implants or stents for example are suitable for other routes of administration.

Oral or parenteral administration is preferred, especially oral administration.

The compounds according to the invention can be transformed to the aforementioned dosage forms. This can take place in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants such as ascorbic acid), colorants (e.g. inorganic pigments, for example iron oxides) and taste and/or odour correctants.

In general, it has proved advantageous, in the case of parenteral administration, to administer amounts of about 0.001 to 1 mg/kg, preferably about 0.01 to 0.5 mg/kg body weight to achieve effective results. For oral application, the dosage is about 0.001 to 2 mg/kg, preferably about 0.001 to 1 mg/kg body weight.

Nevertheless, it may optionally be necessary to deviate from the stated amounts, namely depending on body weight, route of administration, individual response to the active substance, type of preparation and time point or interval when application takes place. Thus, in some cases it may be sufficient to use less than the aforementioned minimum amount, whereas in other cases the stated upper limit must be exceeded. When applying larger amounts, it may be advisable to distribute these in several individual doses throughout the day.

The following practical examples explain the invention. The invention is not limited to the examples.

The percentages in the following tests and examples are percentages by weight, unless stated otherwise; parts are parts by weight. Proportions of solvents, dilution ratios and concentrations for liquid/liquid solutions refer in each case to the volume.

| Abbreviations and acronyms: | |
|---|---|
| abs. | absolute (=dried) |
| aq. | aqueous solution |
| br | broad signal (NMR coupling pattern) |
| δ | shift in the NMR spectrum (stated in ppm) |
| d | doublet (NMR coupling pattern) |
| DCI | direct chemical ionization (in MS) |
| DMAP | 4-N,N-dimethylaminopyridine |
| DMF | dimethylformamide |
| DMSO | dimethyl sulphoxide |
| eq. | equivalent(s) |
| ESI | electrospray ionization (in MS) |
| Et | ethyl |
| h | hour(s) |
| HPLC | high pressure, high performance liquid chromatography |
| HRMS | high resolution mass spectrometry |
| konz. | concentrated |
| LC/MS | liquid chromatography-coupled mass spectrometry |
| LiHMDS | lithium hexamethyldisilazide |
| m | multiplet |
| Me | methyl |
| min | minute(s) |
| MS | mass spectrometry |
| NMR | nuclear magnetic resonance spectrometry |
| Ph | phenyl |
| q | quartet (NMR coupling pattern) |
| quint. | quintet (NMR coupling pattern) |
| RT | room temperature |
| $R_f$ | retention time (in HPLC) |
| s | singulet (NMR coupling pattern) |
| t | triplet (NMR coupling pattern) |
| TFA | trifluoroacetic acid |
| THF | tetrahydrofuran |
| TBTU | (benzotriazol-1-yloxy)bisdimethylaminomethylium fluoroborate |
| UV | ultraviolet spectrometry |
| v/v | ratio by volume (of a solution) |
| XPHOS | dicyclohexyl-(2',4',6'-triisopropylbiphenyl-2-yl)phosphine |

LC/MS and HPLC Methods:

Method 1 (LC-MS):

Instrument: Micromass Quattro Premier with Waters UPLC Acquity; column: Thermo Hypersil GOLD 1.9μ 50×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A oven: 50° C.; flow rate: 0.33 ml/min; UV detection: 210 nm.

Method 2 (LC-MS):

Instrument: Waters ACQUITY SQD UPLC System; column: Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A oven: 50° C.; flow rate: 0.40 ml/min; UV detection: 210-400 nm.

Method 3 (LC-MS):

MS instrument type: Waters (Micromass) Quattro Micro; HPLC instrument type: Agilent 1100 Series; column: Thermo Hypersil GOLD 3μ 20×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A; oven: 50° C.; flow rate: 2 ml/min; UV detection: 210 nm.

Method 4 (LC-MS):

Instrument: Waters ACQUITY SQD UPLC System; column: Waters Acquity UPLC HSS T3 1.8μ 30×2 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A oven: 50° C.; flow rate: 0.60 ml/min; UV detection: 208-400 nm.

Method 5 (LC-MS):

MS instrument: Waters SQD; HPLC instrument: Waters UPLC; column: Zorbax SB-Aq (Agilent), 50 mm×2.1 mm, 1.8 μm; mobile phase A: water+0.025% formic acid, mobile phase B: acetonitrile (ULC)+0.025% formic acid; gradient: 0.0 min 98% A-0.9 min 25% A-1.0 min 5% A-1.4 min 5% A-1.41 min 98% A-1.5 min 98% A; oven: 40° C.; flow rate: 0.600 ml/min; UV detection: DAD; 210 nm.

Method 6 (Preparative HPLC):

Column: Macherey-Nagel VP 50/21 Nucleosil 100-5 C18 Nautilus. Flow rate: 25 ml/min. gradient: A=water+0.1% conc. aq. ammonia, B=methanol, 0 min=30% B, 2 min=30% B, 6 min=100% B, 7 min=100% B, 7 1 min=30% B, 8 min=30% B, flow rate 25 ml/min, UV detection 220 nm.

Method 7 (Preparative HPLC):

Column: Macherey-Nagel VP 50/21 Nucleosil 100-5 C18 Nautilus. Flow rate: 25 ml/min. Gradient: A=acetonitrile, B=water+0.1% formic acid, 0 min 10% A; 2.00 min 10% A; 6.00 min 90% A; 7.00 min 90% A; 7.10 min 10% A; 8 min 10% A; UV detection: 220 nm.

Method 8 (Preparative HPLC):

Column: Nucleodur C18 Gravity 50×200 mm, 10 μm, gradient: A=water+0.1% concentrated aq ammonia, B=methanol, 0 min=30% B, 5 min=30% B, 23 min=100% B, 28 min=1000% B, 28.2 min=30% B, 34 min=30% B, flow rate 110 ml/min, wavelength 220 nm.

Method 9 (Preparative HPLC):

Column: Axia Gemini 5μ C18 110 A, 50×21.5 mm, P/NO: 00B-4435-PO-AX, S/NO: 35997-2, gradient: A=water+0.1% concentrated water Ammonia, B=acetonitrile, 0 min=30% B, 2 min=30% B, 6 min=100% B, 7 min=100% B, 7 1 min=30% B, 8 min=30% B, flow rate 25 ml/min, UV detection 220 nm.

Method 10 (Preparative LCMS):

MS instrument: Waters, HPLC instrument: Waters (column Waters X-Bridge C18, 18 mm×50 mm, 5 μm, mobile phase A: water+0.05% triethylamine, mobile phase B: acetonitrile (ULC)+0.05% triethylamine, gradient: 0.0 min 95% A-0.15 min 95% A-8.0 min 5% A-9.0 min 5% A; flow rate: 40 ml/min; UV detection: DAD; 210-400 nm).

or:

MS instrument: Waters, HPLC instrument: Waters (column Phenomenex Luna 5μ C18(2) 100 A, AXIA Tech. 50×21.2 mm, mobile phase A: water+0.05% formic acid, mobile phase B: acetonitrile (ULC)+0.05% formic acid, gradient: 0.0 min 95% A-0.15 min 95% A-8.0 min 5% A-9.0 min 5% A; flow rate: 40 ml/min; UV detection: DAD; 210-400 nm).

Method 11 (DCI-MS):

(Instrument: Thermo Fisher-Scientific DSQ; chemical ionization; reactant gas $NH_3$; source temperature: 200° C.; ionization energy 70 eV.

Method 12 (MS):

Instrument: Waters ZQ; ionization type: ESI (+); mobile phase; acetonitrile/water.

If compounds according to the invention are purified by preparative HPLC according to the methods described above where the mobile phases contain additives such as trifluoroacetic acid, formic acid or ammonia, the compounds according to the invention may be obtained in salt form, for example as trifluoroacetate, formate or ammonium salt, if the compounds according to the invention contain a functionality which is sufficiently basic or acidic. Such a salt may be converted by various methods known to the person skilled in the art into the corresponding free base or acid, respectively.

Salts may be present in substoichiometric or superstoichiometric amounts, in particular if an amine or a carboxylic acid is present. In addition, in the case of the present imidazopyridines, under acidic conditions there may always be salts present, even in substoichiometric amounts, without this being obvious from the $^1$H NMR, and without particular indication and labelling of these in the respective IUPAC names and structural formulae.

The multiplicities of proton signals in the $^1$H NMR spectra given in the paragraphs below indicate the signal form observed in each case and do not take into account any higher order signal phenomena.

General Working Procedures

Representative Working Procedure 1

Amide Formation Using TBTU as Coupling Agent.

1 equivalent of the carboxylic acid to be coupled (for example Examples 3A, 6A, 11A, 19A, 21A), 1.0-1.5 equivalents of (benzotriazol-1-yloxy)bisdimethylaminomethylium fluoroborate (TBTU) and 4-6 equivalents of 4-methylmorpholine were initially charged in DMF or dichloromethane (about 0.1-0.2 M based on the carboxylic acid to be coupled) and 1.0 to 1.5 equivalents of the amine to be coupled were then added, and the mixture was stirred at RT overnight.

Exemplary work-up of the reaction mixture: Water was added to the reaction solution and the precipitate formed stirred for 0.5-1.0 h, filtered off and washed thoroughly with water and dried under high vacuum overnight. Alternatively, the precipitate or crude reaction mixture was purified further directly by preparative HPLC (RP18 column, mobile phase: acetonitrile/water gradient with addition of 0.1% TFA or 0.1% formic acid) and dried under high vacuum overnight.

Representative Working Procedure 2

Amide Formation Using HATU as Coupling Agent.

1 equivalent of the carboxylic acid to be coupled (for example Example 3A, 6A, 11A, 19A, 21A), 1.2 to 2.5 equivalents of O-(7-azabenzotriazol-1-yl)-N,N,N',N'N'-tetramethyluronium hexafluorophosphate (HATU) and 3 to 4 equivalents of N,N-diisopropylethylamine were initially charged in DMF (about 0.2 M based on the carboxylic acid to be coupled), 1.2 to 2.0 equivalents of the amine to be coupled were added and the mixture was stirred at RT overnight.

Exemplary work-up of the reaction mixture: Water was added to the reaction solution and the precipitate formed stirred for 30 min, filtered off and washed thoroughly with water and dried under high vacuum overnight. Alternatively, either directly after concentration under reduced pressure or after extractive work-up, the crude reaction mixture was purified further by preparative HPLC.

Representative Working Procedure 3

Amide Formation Using the Carbonyl Chloride 1 equivalent of the carbonyl chloride to be coupled (for example, example compound 3A, 6A) was initially charged in THF (about 0.02 to 0.03 M), 1.2 equivalents of the amine to be coupled and 4 equivalents of N,N-diisopropylethylamine were added and the mixture was stirred at RT overnight. The reaction solution was concentrated using a rotary evaporator and re-dissolved in a little acetonitrile, and water was added. The precipitated solid was stirred for about 30 min, filtered off and washed thoroughly with water. Alternatively, the crude reaction product was purified further by preparative HPLC.

STARTING MATERIALS AND INTERMEDIATES

Example 1A

3-[(2,6-Difluorobenzyl)oxy]pyridine-2-amine

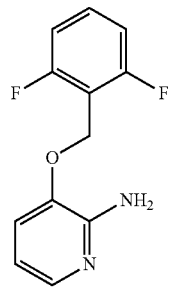 [SMILES: Nc1ncccc1OCc1c(F)cccc1F]

At RT, 51 g of sodium methoxide (953 mmol, 1.05 equivalents) were initially charged in 1000 ml of methanol, 100 g of 2-amino-3-hydroxypyridine (908 mmol, 1 equivalent) were added and the mixture was stirred at RT for another 15 min. The reaction mixture was concentrated under reduced pressure, the residue was taken up in 2500 ml of DMSO and 197 g of 2,6-difluorobenzyl bromide (953 mmol, 1.05 equivalents) were added. After 4 h at RT, the reaction mixture was poured into 20 l of water and stirred for 15 min, the solid was filtered off, washed with 1 l of water, 100 ml of isopropanol and 500 ml of petroleum ether and dried under high vacuum. This gave 171 g of the title compound (78% of theory).

$^1$H NMR (400 MHz, DMSO-$d_6$): δ=5.10 (s, 2H); 5.52 (br. s, 2H), 6.52 (dd, 1H); 7.16-7.21 (m, 3H); 7.49-7.56 (m, 2H).

Example 2A

Ethyl 8-[(2,6-difluorobenzyl)oxy]-2-methylimidazo[1,2-a]pyridine-3-carboxylate

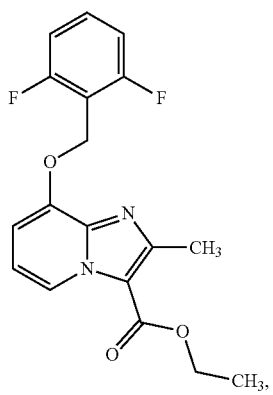 [SMILES: CCOC(=O)c1c(C)nc2c(OCc3c(F)cccc3F)cccn12]

170 g of 3-[(2,6-difluorobenzyl)oxy]pyridine-2-amine (Example 1A; 719 mmol, 1 equivalent) were initially charged in 3800 ml of ethanol, and 151 g of powdered molecular sieve 3 Å and 623 g of ethyl 2-chloroacetoacetate (3.6 mol, 5 equivalents) were added. The mixture was heated at reflux for 24 h and then filtered off through kieselguhr and concentrated under reduced pressure. After standing for a relatively long time (48 h) at RT a solid precipitated out. It was filtered off, stirred three times with a little isopropanol and then filtered off each time and finally washed with diethyl ether. This gave 60.8 g (23.4% of theory) of the title compound. The combined mother liquor of the filtration steps was chromatographed on silica gel using cyclohexane/diethyl ether as mobile phase, and this gave a further 46.5 g (18.2% of theory; total yield: 41.6% of theory) of the title compound.

LC-MS (Method 2): $R_t$=1.01 min

MS (ESpos): m/z=347 (M+H)$^+$ $^1$H NMR (400 MHz, DMSO-d$_6$): δ=1.36 (t, 3H); 2.54 (s, 3H; obscured by DMSO signal); 4.36 (q, 2H); 5.33 (s, 2H); 7.11 (t, 1H); 7.18-7.27 (m, 3H); 7.59 (quint, 1H); 8.88 (d, 1H).

Example 3A

8-[(2,6-Difluorobenzyl)oxy]-2-methylimidazo[1,2-a]pyridine-3-carboxylic acid

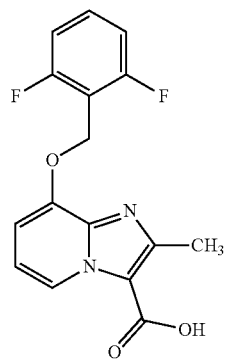 [SMILES: Cc1nc2c(OCc3c(F)cccc3F)cccn2c1C(=O)O]

107 g of ethyl 8-[(2,6-difluorobenzyl)oxy]-2-methylimidazo[1,2-a]pyridine-3-carboxylate (Example 2A; 300 mmol, 1 equivalent) were dissolved in 2.8 l of THF/methanol (1:1), 1.5 l of 1 N aqueous lithium hydroxide solution (1.5 mol, 5 equivalents) were added and the mixture was stirred at RT for 16 h. The organic solvents were removed under reduced pressure and the resulting aqueous solution was adjusted in an ice bath to pH 3-4 using 1 N aqueous hydrochloric acid. The resulting solid was filtered off, washed with water and isopropanol and dried under reduced pressure. This gave 92 g (95% of theory) of the title compound.

LC-MS (Method 2): $R_t$=0.62 min

MS (ESpos): m/z=319.1 (M+H)$^+$ $^1$H NMR (400 MHz, DMSO-d$_6$): δ=2.55 (s, 3H; superimposed by DMSO signal); 5.32 (s, 2H); 7.01 (t, 1H); 7.09 (d, 1H); 7.23 (t, 2H); 7.59 (q, 1H); 9.01 (d, 1H).

Example 4A 3-(Cyclohexylmethoxy)pyridine-2-amine

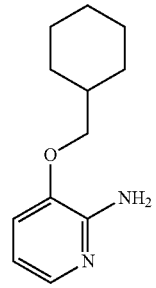

At RT, 96 g of aqueous sodium hydroxide solution (45%; 1081 mmol, 1 equivalent) were initially charged in 1170 ml of methanol, 119 g of 2-amino-3-hydroxypyridine (1080 mmol, 1 equivalent) were added and the mixture was stirred at RT for 10 min. The reaction mixture was concentrated under reduced pressure, the residue was taken up in 2900 ml of DMSO and 101 g of cyclohexylmethyl bromide (1135 mmol, 1.05 equivalents) were added. After 16 h at RT, the reaction mixture was stirred into 6 l of water, the aqueous solution was extracted twice with in each case 2 l of ethyl acetate, the combined organic phases were washed with in each case 1 l of saturated aqueous sodium bicarbonate solution and water, dried, filtered and concentrated. The residue was triturated with 500 ml of n-pentane, filtered off and dried under reduced pressure. This gave 130 g (58.3% of theory) of the title compound.

LC-MS (Method 3): $R_t$=1.41 min

MS (ESpos): m/z=207.1 (M+H)$^+$

Example 5A

Ethyl 8-(cyclohexylmethoxy)-2-methylimidazo[1,2-a]pyridine-3-carboxylate

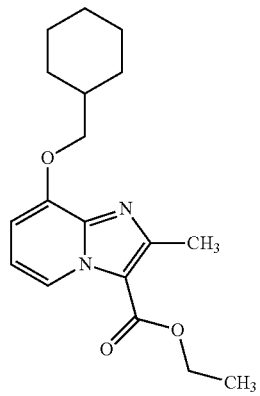 [SMILES: CCOC(=O)c1c(C)nc2c(OCC3CCCCC3)cccn12]

130 g of 3-(cyclohexylmethoxy)pyridine-2-amine (Example 4A; 630 mmol, 1 equivalent) were initially charged in 3950 ml of ethanol, and 436 ml of ethyl 2-chloroacetoacetate (3.2 mol, 5 equivalents) were added. The resulting reaction mixture was heated under reflux for 24 h and then concentrated under reduced pressure. The crude product obtained in this manner was chromatographed on silica gel using cyclohexane/diethyl ether as mobile phase, giving 66.2 g (33.2% of theory) of the title compound.

LC-MS (Method 2): $R_t$=1.17 min
MS (ESpos): m/z=317.1 (M+H)$^+$
1H NMR (400 MHz, DMSO-$d_6$): δ=1.02-1.31 (m, 5H); 1.36 (t, 3H); 1.64-1.77 (m, 3H); 1.79-1.90 (m, 3H); 2.60 (s, 3H); 3.97 (d, 2H); 4.35 (q, 2H); 6.95 (d, 1H); 7.03 (t, 1H); 8.81 (d, 1H).

Example 6A 8-(Cyclohexylmethoxy)-2-methylimidazo[1,2-a]pyridine-3-carboxylic acid

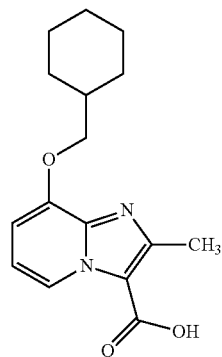 [SMILES: Cc1nc2c(OCC3CCCCC3)cccn2c1C(=O)O]

50 g of ethyl 8-(cyclohexylmethoxy)-2-methylimidazo[1,2-a]pyridine-3-carboxylate (Example 5A; 158 mmol, 1 equivalent) were dissolved in 600 ml of dioxane, 790 ml of 2 N aqueous sodium hydroxide solution (1.58 mol, 10 equivalents) were added and the mixture was stirred at RT for 16 h. Then 316 ml of 6 N aqueous hydrochloric acid were added, and the mixture was reduced to about ⅓ of the total volume. The resulting solid was filtered off, washed with water and tert-butyl methyl ether and dried under reduced pressure. This gave 35 g (74% of theory) of the title compound.

LC-MS (Method 2): $R_t$=0.81 min
MS (ESpos): m/z=289.0 (M+H)$^+$
$^1$H NMR (400 MHz, DMSO-$d_6$): δ=1.03-1.44 (m, 5H); 1.64-1.78 (m, 3H); 1.81-1.92 (m, 3H); 2.69 (s, 3H); 4.07 (d, 2H); 7.30-7.36 (m, 2H); 9.01 (d, 1H).

Example 7A

5-Chloro-2-nitropyridin-3-ol

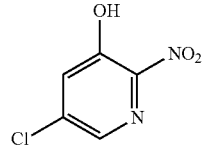 [SMILES: O=[N+]([O-])c1ncc(Cl)cc1O]

With ice cooling, 30 g of 5-chloropyridin-3-ol (232 mmol, 1 equivalent) were dissolved in 228 ml of concentrated sulphuric acid, and, at 0° C., 24 ml of concentrated nitric acid were added slowly. The reaction was warmed to RT and stirred overnight. The reaction mixture was stirred into an ice/water mixture and it was stirred for another 30 min The solid was filtered off, washed with cold water and air-dried. This gave 33 g (82% of theory) of the title compound, which were used without further purification for the next reaction.

LC-MS (Method 2): $R_t$=0.60 min
MS (ESneg): m/z=172.9/174.9 (M−H)$^-$
$^1$H NMR (400 MHz, DMSO-$d_6$): δ=7.71 (d, 1H); 8.10 (d, 1H); 12.14 (br. 1H).

Example 8A

5-Chloro-3-[(2,6-difluorobenzyl)oxy]-2-nitropyridine

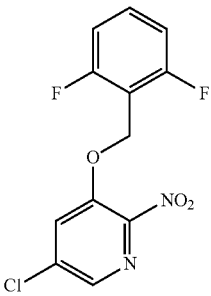 [SMILES: O=[N+]([O-])c1ncc(Cl)cc1OCc1c(F)cccc1F]

33 g of 5-chloro-2-nitropyridin-3-ol (Example 12A; 189 mmol, 1 equivalent) and 61.6 g of caesium carbonate (189 mmol, 1 equivalent) were initially charged in 528 ml of DMF, 40.4 g of 2,6-difluorobenzyl bromide (189 mmol, 1 equivalent) were added and the mixture was stirred at RT overnight. The reaction mixture was stirred into a water/1N aqueous hydrochloric acid mixture. The solid obtained was filtered off, washed with water and air-dried. This gave 54.9 g (97% of theory) of the title compound.

$^1$H NMR (400 MHz, DMSO-$d_6$): δ=5.46 (s, 2H); 7.22 (t, 2H); 7.58 (q, 1H); 8.28 (d, 1H); 8.47 (d, 1H).

Example 9A

5-Chloro-3-[(2,6-difluorobenzyl)oxy]pyridine-2-amine

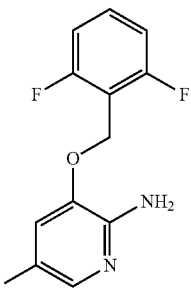

59.7 g of 5-chloro-3-[(2,6-difluorobenzyl)oxy]-2-nitropyridine (Example 13A; 199 mmol, 1 equivalent) were initially charged in 600 ml of ethanol, 34.4 g of iron powder (616 mmol, 3.1 equivalents) were added and the mixture was heated to reflux. 152 ml of concentrated hydrochloric acid were slowly added dropwise and the mixture was boiled at reflux for a further 30 min. The reaction mixture was cooled and stirred into an ice/water mixture. The resulting mixture was adjusted to pH 5 using sodium acetate, the solid obtained was filtered off, washed with water and air-dried and then dried under reduced pressure at 50° C. This gave 52.7 g (98% of theory) of the title compound.

LC-MS (Method 2): $R_t$=0.93 min

MS (ESpos): m/z=271.1/273.1 (M+H)$^+$ $^1$H NMR (400 MHz, DMSO-d$_6$): δ=5.14 (s, 2H); 5.82 (br. s, 2H); 7.20 (t, 2H); 7.35 (d, 1H); 7.55 (q, 1H); 7.56 (d, 1H).

Example 10A

Ethyl 6-chloro-8-[(2,6-difluorobenzyl)oxy]-2-methylimidazo[1,2-a]pyridine-3-carboxylate

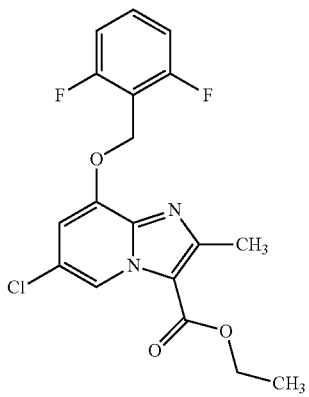 [SMILES: CCOC(=O)c1c(C)nc2c(OCc3c(F)cccc3F)cc(Cl)cn12]

40 g of 5-chloro-3-[(2,6-difluorobenzyl)oxy]pyridine-2-amine (Example 14A; 147.8 mmol; 1 equivalent) were initially charged in 800 ml of ethanol, 30 g of powdered molecular sieve 3A and 128 g of ethyl 2-chloroacetoacetate (739 mmol, 5 equivalents) were added and the mixture was heated at reflux overnight. The reaction mixture was concentrated and the residue was taken up in ethyl acetate and filtered. The ethyl acetate phase was washed with water, dried, filtered and concentrated. This gave 44 g (78% of theory) of the title compound.

LC-MS (Method 2): $R_t$=1.27 min

MS (ESpos): m/z=381.2/383.2 (M+H)$^+$ $^1$H NMR (400 MHz, DMSO-d$_6$): δ=1.36 (t, 3H); 2.54 (s, 3H; obscured by DMSO signal); 4.37 (q, 2H); 5.36 (s, 2H); 7.26 (t, 2H); 7.38 (d, 1H); 7.62 (q, 1H); 8.92 (d, 1H).

Example 11A

6-Chloro-8-[(2,6-difluorobenzyl)oxy]-2-methylimidazo[1,2-a]pyridine-3-carboxylic acid

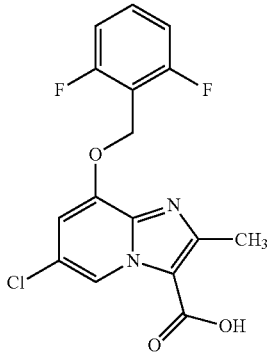 [SMILES: Cc1nc2c(OCc3c(F)cccc3F)cc(Cl)cn2c1C(=O)O]

44 g of ethyl 6-chloro-8-[(2,6-difluorobenzyl)oxy]-2-methylimidazo[1,2-a]pyridine-3-carboxylate (Example 15A; 115.5 mmol, 1 equivalent) were dissolved in 550 ml of THF and 700 ml of methanol, 13.8 g of lithium hydroxide (dissolved in 150 ml of water; 577 mmol, 5 equivalents) were added and the mixture was stirred at RT overnight. 1 N aqueous hydrochloric acid was added to the reaction mixture, and the mixture was concentrated. The solid obtained was filtered off and washed with water. This gave 34 g of the title compound (84% of theory).

LC-MS (Method 1): $R_t$=1.03 min

MS (ESpos): m/z=353.0/355.0 (M+H)$^+$ $^1$H NMR (400 MHz, DMSO-d$_6$): δ=2.54 (s, 3H; superimposed by DMSO signal); 5.36 (s, 2H); 7.26 (t, 2H); 7.34 (d, 1H); 7.61 (q, 1H); 8.99 (d, 1H); 13.36 (br. s, 1H).

Example 12A

5-Bromo-3-[(2,6-difluorobenzyl)oxy]pyridine-2-amine

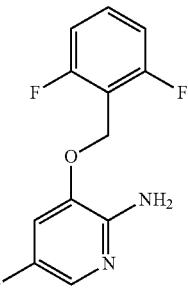

32.6 g of 3-[(2,6-difluorobenzyl)oxy]pyridine-2-amine (Example 1A; 138 mmol, 1 equivalent) were suspended in 552 ml of 10% strength aqueous sulphuric acid, and the mixture was cooled to 0° C. 8.5 ml of bromine (165 mmol, 1.2 equivalents) were dissolved in 85 ml of acetic acid and then, over a period of 90 min, added dropwise to the ice-cooled reaction solution. After the dropwise addition had ended, the mixture was stirred at 0° C. for 90 min and then diluted with 600 ml of ethyl acetate, and the aqueous phase was separated off. The aqueous phase was re-extracted with ethyl acetate. The organic phases were combined, washed with saturated aqueous sodium bicarbonate solution, dried and concentrated. The residue was dissolved in dichloromethane and chromatographed on silica gel (petroleum ether/ethyl acetate gradient as mobile phase). This gave 24 g (55% of theory) of the title compound.

LC-MS (Method 2): $R_t$=0.96 min

MS (ESpos): m/z=315.1/317.1 (M+H)$^+$ $^1$H NMR (400 MHz, DMSO-d$_6$): δ=5.14 (s, 2H); 5.83 (br. s, 2H); 7.20 (t, 2H); 7.42 (d, 1H); 7.54 (q, 1H); 7.62 (d, 1H).

Example 13A

Ethyl 6-bromo-8-[(2,6-difluorobenzyl)oxy]-2-methylimidazo[1,2-a]pyridine-3-carboxylate

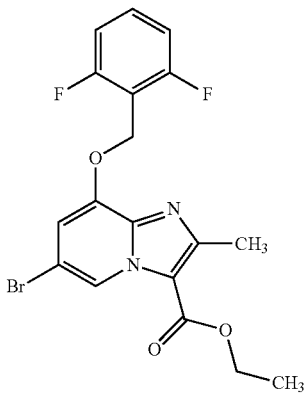

24 g of 5-bromo-3-[(2,6-difluorobenzyl)oxy]pyridine-2-amine (Example 17A; 76.2 mmol; 1 equivalent) were initially charged in 400 ml of ethanol, 16 g of powdered molecular sieve 3 Å and 52.7 ml of ethyl 2-chloroacetoacetate (380.8 mmol; 5 equivalents) were added and the mixture was heated at reflux overnight. A further 8 g of molecular sieve were added, and the mixture was heated at reflux for a further 24 h. The reaction mixture was concentrated and the residue was taken up in dichloromethane and chromatographed on silica gel (dichloromethane/methanol 20:1 as mobile phase). The product-containing fractions were concentrated and the residue was stirred with 100 ml of diethyl ether for 30 min, and the product was filtered off, washed with a little diethyl ether and dried. This gave 15 g (45% of theory) of the title compound.

LC-MS (Method 1): $R_t$=1.43 min

MS (ESpos): m/z=414.9/416.8 (M+H)$^+$ $^1$H NMR (400 MHz, DMSO-$d_6$): δ=1.36 (t, 3H); 2.54 (s, 3H; obscured by DMSO signal); 4.37 (q, 2H); 5.36 (s, 2H); 7.25 (t, 2H); 7.42 (d, 1H); 7.61 (q, 1H); 9.00 (d, 1H).

Example 14A 3-(Benzyloxy)-5-bromopyridine-2-amine

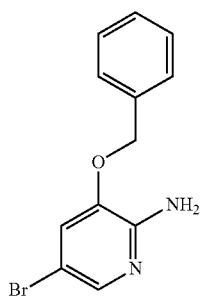 [SMILES: Nc1ncc(Br)cc1OCc1ccccc1]

200 g (1 mol) of 2-amino-3-benzyloxypyridine were initially charged in 4 l of dichloromethane, and a solution of 62 ml (1.2 mol) of bromine in 620 ml of dichloromethane was added at 0° C. over a period of 30 min. After the addition had ended, the reaction solution was stirred at 0° C. for 60 min. About 4 l of saturated aqueous sodium bicarbonate solution were then added to the mixture. The organic phase was separated off and concentrated. The residue was purified by silica gel column chromatography (petroleum ether:ethyl acetate 6:4) and the product fractions were concentrated. This gave 214 g (77% of theory) of the title compound.

LC-MS (Method 2): $R_t$=0.92 min

MS (ESpos): m/z=279 (M+H)$^+$ $^1$H NMR (400 MHz, DMSO-$d_6$): δ=5.16 (s, 2H), 5.94-6.00 (m, 2H), 7.26-7.29 (m, 1H), 7.31-7.36 (m, 1H), 7.37-7.43 (m, 2H), 7.47-7.52 (m, 2H), 7.57-7.59 (m, 1H).

Example 15A

Ethyl 8-(benzyloxy)-6-bromo-2-methylimidazo[1,2-a]pyridine-3-carboxylate

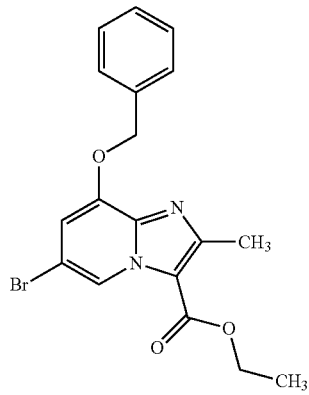 [SMILES: CCOC(=O)c1c(C)nc2c(OCc3ccccc3)cc(Br)cn12]

Under argon, 200 g (0.72 mol) of 3-(benzyloxy)-5-bromopyridine-2-amine, 590 g (3.58 mol) of ethyl 2-chloroacetoacetate and 436 g of 3 A molecular sieve were suspended in 6 l of ethanol and boiled at reflux for 72 h. The reaction mixture was filtered off through kieselguhr and concentrated. The residue was purified by silica gel chromatography (petroleum ether:ethyl acetate 9:1, then 6:4) and the product fractions were concentrated. This gave 221 g (79% of theory) of the target compound.

LC-MS (Method 4): $R_t$=1.31 min

MS (ESpos): m/z=389 (M+H)$^+$ $^1$H NMR (400 MHz, DMSO-d$_6$): δ=1.36 (t, 3H), 2.58 (s, 3H), 4.32-4.41 (m, 2H), 5.33 (s, 2H), 7.28-7.32 (m, 1H), 7.36-7.47 (m, 3H), 7.49-7.54 (m, 2H), 8.98 (d, 1H).

Example 16A

Ethyl 8-(benzyloxy)-2,6-dimethylimidazo[1,2-a]pyridine-3-carboxylate

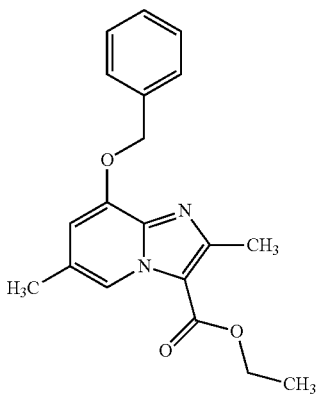 [SMILES: CCOC(=O)c1c(C)nc2c(OCc3ccccc3)cc(C)cn12]

Under argon, 105 g (270 mmol) of ethyl 8-(benzyloxy)-6-bromo-2-methylimidazo[1,2-a]pyridine-3-carboxylate Example 15A were suspended in 4.2 l of 1,4-dioxane, 135.4 g (539 mmol, purity 50%) of trimethylboroxine, 31.2 g (27 mmol) of tetrakis(triphenylphosphine)palladium(0) and 78.3 g (566 mmol) of potassium carbonate were added in succession and the mixture was stirred under reflux for 8 h. The reaction mixture, cooled to RT, was filtered off from the precipitate over silica gel and the filtrate was concentrated. The residue was dissolved in dichloromethane and purified by silica gel chromatography (dichloromethane:ethyl acetate=9:1). This gave 74 g (84.6% of theory; purity 100%) of the target compound.

LC-MS (Method 4): R$_t$=1.06 min

MS (ESpos): m/z=325 (M+H)$^+$ $^1$H NMR (400 MHz, DMSO-d$_6$): δ=1.35 (t, 3H), 2.34 (br. s, 3H), 2.56 (s, 3H), 4.31-4.38 (m, 2H), 5.28 (br. s, 2H), 6.99-7.01 (m, 1H), 7.35-7.47 (m, 3H), 7.49-7.54 (m, 2H), 8.68-8.70 (m, 1H).

Example 17A

Ethyl 8-hydroxy-2,6-dimethylimidazo[1,2-a]pyridine-3-carboxylate

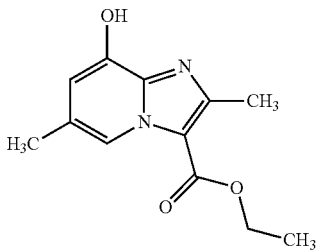 [SMILES: CCOC(=O)c1c(C)nc2c(O)cc(C)cn12]

74 g (228 mmol) of ethyl 8-(benzyloxy)-2,6-dimethylimidazo[1,2-a]pyridine-3-carboxylate Example 16A were initially charged in 1254 ml of dichloromethane and 251 ml of ethanol, and 20.1 g 10% palladium on activated carbon (moistened with water 50%) were added under argon. The reaction mixture was hydrogenated overnight at RT and atmospheric pressure. The reaction mixture was filtered off through kieselguhr and concentrated. The crude product was purified by silica gel chromatography (dichloromethane:methanol=95:5). This gave 50.4 g (94% of theory) of the target compound.

DCI-MS: (Method 11) (ESpos): m/z=235.2 (M+H)$^+$ $^1$H NMR (400 MHz, DMSO-d$_6$): δ=1.35 (t, 3H), 2.27 (s, 3H), 2.58 (s, 3H), 4.30-4.38 (m, 2H), 6.65 (d, 1H), 8.59 (s, 1H), 10.57 (br. s, 1H).

Example 18A

Ethyl 8-[(2,6-difluorobenzyl)oxy]-2,6-dimethylimidazo[1,2-a]pyridine-3-carboxylate

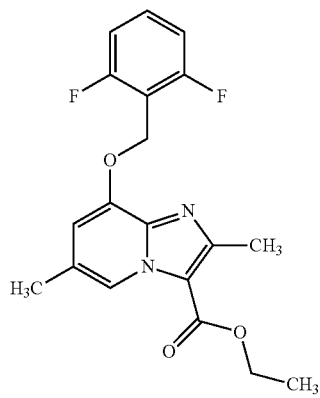 [SMILES: CCOC(=O)c1c(C)nc2c(OCc3c(F)cccc3F)cc(C)cn12]

20.00 g (85.38 mmol) of ethyl 8-hydroxy-2,6-dimethylimidazo[1,2-a]pyridine-3-carboxylate Example 17A were initially charged with 19.44 g (93.91 mmol) of 2,6-difluorobenzyl bromide and 61.20 g (187.83 mmol) of caesium carbonate in 1.18 l of DMF and stirred at 60° C. for 5 h. The flask content was poured 6.4 l of 10% strength aqueous sodium chloride solution and extracted twice with ethyl acetate. The combined organic phases were washed once with 854 ml of 10% strength aqueous sodium chloride solution, dried, evaporated and dried under high vacuum at RT overnight. This gave 28.2 g (92% of theory; purity about 90%) of the title compound.

LC-MS (Method 2): R$_t$=1.05 min

MS (ESpos): m/z=361.1 (M+H)$^+$ $^1$H NMR (400 MHz, DMSO-d$_6$): δ=1.38 (t, 3H); 2.36 (s, 3H); 4.35 (q, 2H); 5.30 (s, 2H); 7.10 (s, 1H); 7.23 (t, 2H); 7.59 (q, 1H); 8.70 (s, 1H).

Example 19A

8-[(2,6-Difluorobenzyl)oxy]-2,6-dimethylimidazo[1,2-a]pyridine-3-carboxylic acid

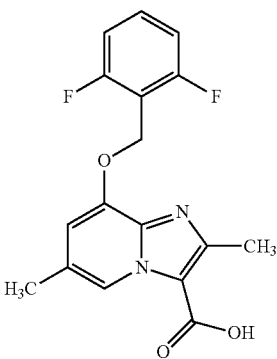

220 mg of ethyl 8-[(2,6-difluorobenzyl)oxy]-2,6-dimethylimidazo[1,2-a]pyridine-3-carboxylate (Example 20A; 0.524 mmol, 1 equivalent) were dissolved in 7 ml of THF/methanol 1:1, 2.6 ml of 1 N aqueous lithium hydroxide solution (2.6 mmol, 5 equivalents) were added and the mixture was stirred at RT for 16 h. The reaction mixture was concentrated and the residue was acidified with 1N aqueous hydrochloric acid. The solid obtained was stirred, filtered off, washed with water and dried under reduced pressure. This gave 120 mg of the title compound (60% of theory).

LC-MS (Method 2): $R_t$=0.68 min
MS (ESpos): m/z=333.1 (M+H)$^+$
$^1$H NMR (400 MHz, DMSO-d$_6$): δ=2.34 (s, 3H); 5.28 (s, 2H); 7.09 (s, 1H); 7.23 (t, 2H); 7.58 (q, 1H); 8.76 (s, 1H); 13.1 (br. s, 1H).

Example 20A

Ethyl 2,6-dimethyl-8-[(2,3,6-trifluorobenzyl)oxy]imidazo[1,2-a]pyridine-3-carboxylate

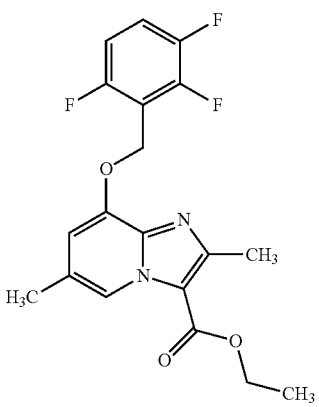 [SMILES: CCOC(=O)c1c(C)nc2c(OCc3c(F)ccc(F)c3F)cc(C)cn12]

3.00 g (12.81 mmol) of ethyl 8-hydroxy-2,6-dimethylimidazo[1,2-a]pyridine-3-carboxylate Example 17A, 3.27 g (14.1 mmol) of 2-(bromomethyl)-1,3,4-trifluorobenzene and 9.18 g (28.17 mmol) of caesium carbonate were initially charged in 183 ml of dry DMF and heated for 30 min in an oil bath warmed to 60° C. About 1.8 l of water were added to the reaction mixture, the mixture was stirred for 30 min and the solid was filtered off, washed with water and dried under reduced pressure. This gave 5.07 g of the title compound (99% of theory; purity about 96%).

LC-MS (Method 2): $R_t$=1.14 min
MS (ESpos): m/z=379 (M+H)$^+$
$^1$H NMR (400 MHz, DMSO-d$_6$): δ=1.35 (t, 3H); 2.36 (s, 3H); 2.55 (s, 3H; superimposed by DMSO signal); 4.36 (q, 2H); 5.35 (s, 2H); 7.09 (s, 1H); 7.22-7.32 (m, 1H); 7.60-7.73 (m, 1H); 8.72 (s, 1H).

Example 21A 2,6-Dimethyl-8-[(2,3,6-trifluorobenzyl)oxy]imidazo[1,2-a]pyridine-3-carboxylic acid

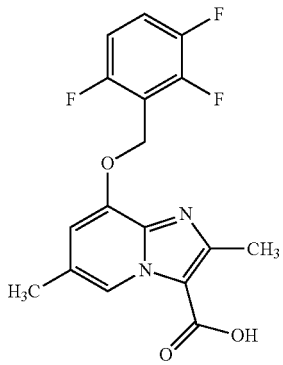

5.07 g (12.87 mmol) of ethyl 2,6-dimethyl-8-[(2,3,6-trifluorobenzyl)oxy]imidazo[1,2-a]pyridine-3-carboxylate Example 20A were dissolved in 275 ml of THF/methanol (5/1), 64.4 ml of 1 N aqueous lithium hydroxide solution were added and the mixture was stirred at 40° C. for 3.5 h. At 0° C., the reaction mixture was acidified to about pH 4 with 6 N aqueous hydrochloric acid and concentrated. The solid formed was filtered off, washed with water and dried under reduced pressure. This gave 4.77 g (98% of theory; purity about 93%) of the title compound.

LC-MS (Method 2): $R_t$=0.72 min
MS (ESpos): m/z=351 (M+H)$^+$
$^1$H NMR (400 MHz, DMSO-d$_6$): δ=2.37 (s, 3H); 2.54 (s, 3H; superimposed by DMSO signal); 5.36 (s, 2H); 7.11 (s, 1H); 7.25-7.33 (m, 1H); 7.61-7.73 (m, 1H); 8.78 (s, 1H); 13.10 (br. s, 1H).

Example 22A

Methyl 3-amino-4,4,4-trifluorobutanoate hydrochloride

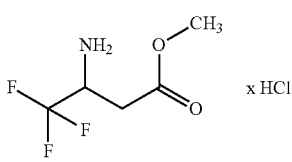

1.5 g of 3-amino-4,4,4-trifluorobutanoic acid (9.55 mmol, 1 equivalent) were initially charged in 18 ml of methanol which had been saturated with hydrogen chloride, and the mixture was stirred under reflux for 4 h. The reaction solution was then concentrated, evaporated repeatedly with dichloromethane and dried under reduced pressure. This gave 1.86 g (94% of theory) of the title compound.

DCI-MS (Method 11): MS (ESpos): m/z=172 (M−HCl+H)$^+$ $^1$H-NMR (400 MHz, DMSO-d$_6$): δ=2.88-3.07 (m, 2H), 3.69 (s, 3H), 4.44-4.57 (m, 1H), 9.10 (br s, 2H).

Example 23A

Methyl 2-amino-4,4,4-trifluorobutanoate hydrochloride

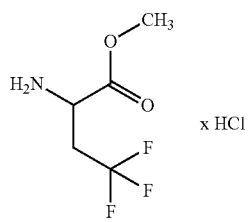

1.186 g (6.127 mmol) of 2-amino-4,4,4-trifluorobutanoic acid hydrochloride (1:1) were initially charged in 11.6 ml of methanol which had been saturated with hydrogen chloride, and the mixture was stirred under reflux for 4 h. The reaction solution was concentrated and dried under high vacuum. This gave 1.275 g of the target compound (100% of theory).

DCI-MS (Method 11): MS (ESpos): m/z=172 (M−HCl+H)$^+$ $^1$H-NMR (400 MHz, DMSO-d$_6$): δ=2.90-3.08 (m, 2H), 3.78 (s, 3H), 3.41 (t, 1H), 8.89 (br. s, 3H).

The example compounds shown in Table 1A were prepared analogously to Example 23A by reacting hydrogen chloride in methanol with the appropriate commercially available amino acids under the reaction conditions described:

TABLE 1A

| Example | IUPAC name/structure (yield) | Analytical data |
|---|---|---|
| 24A | methyl 5,5,5-trifluoronorvalinate hydrochloride (1:1)<br>H$_2$N−CH(COOCH$_3$)−CH$_2$−CH$_2$−CF$_3$ · xHCl<br>(94% of theory) | DCI-MS (Method 12):<br>MS (ESpos): m/z = 186 (M—HCl + H)$^+$ |
| 25A | methyl-6,6,6-trifluoronorleucinate hydrochloride (1:1)<br>H$_2$N−CH(COOCH$_3$)−CH$_2$−CH$_2$−CH$_2$−CF$_3$ · xHCl<br>(100% of theory) | DCI-MS (Method 11):<br>MS (ESpos): m/z = 200 (M—HCl + H)$^+$<br>$^1$H-NMR (400 MHz, DMSO-d$_6$): δ = 1.48-1.73 (m, 2H), 1.82-1.96 (m, 2H), 2.24-2.38 (m, 2H), 3.76 (s, 3H), 4.06-4.12 (m, 1H), 8.54-8.70 (br s, 3H). |

Example Compounds

Example 1 rac-Methyl [({8-[(2,6-difluorobenzyl)oxy]-2-methylimidazo[1,2-a]pyridin-3-yl}carbonyl)amino]-(4-fluorophenyl)acetate

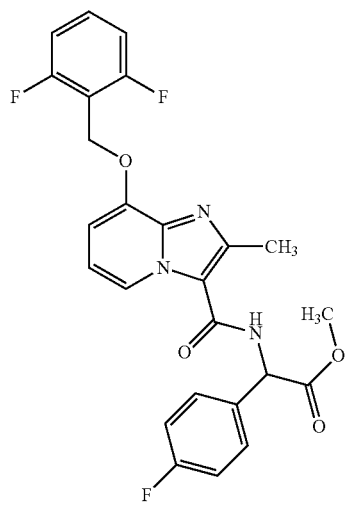 [SMILES: COC(=O)C(NC(=O)c1c(C)nc2c(OCc3c(F)cccc3F)cccn12)c1ccc(Cl)cc1]

Under argon, 750 mg of 8-[(2,6-difluorobenzyl)oxy]-2-methylimidazo[1,2-a]pyridine-3-carboxylic acid Example 3A (2.36 mmol, 1 equivalent) were suspended in 15 ml of DMF, and 1.13 g of (benzotriazol-1-yloxy)bisdimethylaminomethylium fluoroborate (TBTU, 3.54 mmol, 1.5 equivalents), 1.3 ml of 4-methylmorpholine (1.19 g, 11.78 mmol, 5 equivalents) and 517 mg of methyl amino(4-fluorophenyl)acetate (2.83 mmol, 1.2 equivalents, prepared according to Merck and Co., Inc, U.S. Pat. No. 5,691,336 A1, 1997) were added in succession. The mixture was stirred at RT overnight, and about 150 ml of water were then added. The solid obtained was filtered off, washed thoroughly with water and with a little diethyl ether and dried under reduced pressure. This gave 990 mg (84% of theory; purity: 97%) of the title compound.

LC-MS (Method 2): R$_t$=1.04 min

MS (ESpos): m/z=484.2 (M+H)$^+$ $^1$H-NMR (400 MHz, DMSO-d$_6$): δ=3.68 (s, 3H), 5.31 (s, 2H), 5.69 (d, 1H), 6.95 (t, 1H), 7.03 (d, 1H), 7.19-7.29 (m, 4H), 7.53-7.63 (m, 3H), 8.53 (d, 1H), 8.72 (d, 1H), [further signal hidden under DMSO peak].

The examples shown in Table 1 were prepared by reacting 8-[(2,6-difluorobenzyl)oxy]-2-methylimidazo[1,2-a]pyridine-3-carboxylic acid (Example 3A) with the appropriate amines, prepared as described above or commercially available, (1.0-1.5 equivalents) and 4-methylmorpholine (2-6 equivalents) under the reaction conditions described in the General Working Procedure 1.

Exemplary work-ups of the reaction mixture:

Water was added to the reaction solution and the precipitate obtained was stirred for another 0.5-1.0 h, filtered off, washed thoroughly with water and dried under high vacuum overnight.

Alternatively, the precipitate or the crude reaction mixture was diluted (water/THF) and directly purified further by preparative HPLC (RP18 column, mobile phase: acetonitrile/ water gradient with addition of 0.1% TFA or 0.1% formic acid) and dried under high vacuum overnight. If appropriate, the fractions, concentrated on a rotary evaporator, were taken up in dichloromethane and washed twice with saturated aqueous sodium bicarbonate solution. The combined aqueous phases were re-extracted twice with dichloromethane. The combined organic phases were dried over sodium sulphate, filtered and concentrated on a rotary evaporator.

Alternatively, the reaction solution was diluted with dichloromethane. The reaction solution was then washed twice with saturated aqueous sodium bicarbonate solution, once with water and once with aqueous saturated sodium chloride solution, dried over sodium sulphate, filtered and concentrated on a rotary evaporator. The residue was purified on a silica gel cartridge (mobile phases: cyclohexane/ethyl acetate gradient or dichloromethane/methanol gradient).

TABLE 1

| Example | IUPAC-Name/Structure (Yield) | Analytical data |
| --- | --- | --- |
| 2 | rac-Methyl (4-chlorophenyl)[({8-[(2,6-difluorobenzyl)oxy]-2-methylimidazo[1,2-a]pyridin-3-yl}carbonyl)amino]acetate<br />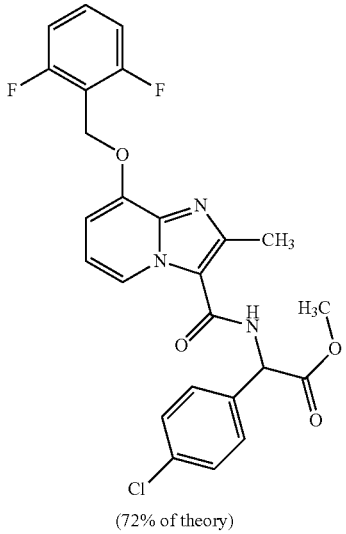<br />(72% of theory) | LC-MS (Method 2): $R_t$ = 1.10 min<br />MS (ESpos): m/z = 500.3 (M + H)$^+$<br />$^1$H-NMR (400 MHz, DMSO-d$_6$):<br />δ = 3.69 (s, 3H), 5.31 (s, 2H), 5.70 (d, 1H), 6.95 (t, 1H), 7.04 (d, 1H), 7.23 (t, 2H), 7.44-7.51 (m, 2H), 7.52-7.64 (m, 3H), 8.53 (d, 1H), 8.74 (d, 1H), [further signal hidden under DMSO peak]. |
| 3 | 8-[(2,6-Difluorobenzyl)oxy]-2-methyl-N-[(3R)-2-oxotetrahydrofuran-3-yl]imidazo[1,2-a]pyridine-3-carboxamide<br />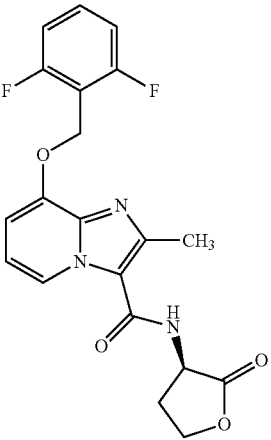 [SMILES: Cc1nc2c(OCc3c(F)cccc3F)cccn2c1C(=O)N[C@@H]1CCOC1=O]<br />(79% of theory; purity: 97%) | LC-MS (Method 2): $R_t$ = 0.75 min<br />MS (ESpos): m/z = 402.2 (M + H)$^+$<br />$^1$H-NMR (400 MHz, DMSO-d$_6$):<br />δ = 2.30-2.45 (m, 1H), 4.25-4.35 (m, 1H), 4.39-4.47 (m, 1H), 4.78-4.89 (m, 1H), 5.31 (s, 2H), 6.97 (t, 1H), 7.06 (d, 1H), 7.24 (t, 2H), 7.54-7.64 (m, 1H), 8.29 (d, 1H), 8.65 (d, 1H), [further signal hidden under DMSO peak]. |

TABLE 1-continued

| Example | IUPAC-Name/Structure (Yield) | Analytical data |
|---|---|---|
| 4 | rac-Methyl 3-[({8-[(2,6-difluorobenzyl)oxy]-2-methylimidazo[1,2-a]pyridin-3-yl}carbonyl)amino]butanoate 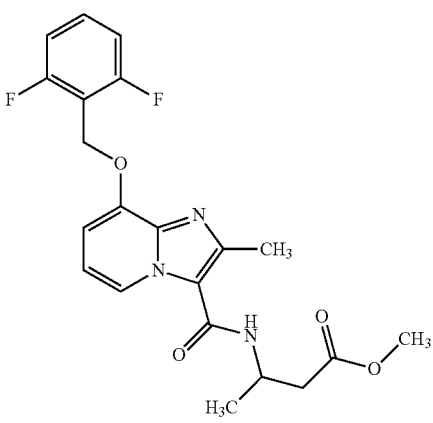 [SMILES: COC(=O)CC(C)NC(=O)c1c(C)nc2c(OCc3c(F)cccc3F)cccn12] (86% of theory; purity: 97%) | LC-MS (Method 2): $R_t$ = 0.81 min<br>MS (ESpos): m/z = 418.3 (M + H)$^+$<br>$^1$H-NMR (400 MHz, DMSO-d$_6$):<br>δ = 1.23 (d, 3H), 2.47 (s, 3H), 2.57-2.73 (m, 2H), 3.61 (s, 3H), 4.33-4.48 (m, 1H), 5.30 (s, 2H), 6.92 (t, 1H), 7.01 (d, 1H), 7.23 (t, 2H), 7.54-7.64 (m, 1H), 7.83 (d, 1H), 8.56 (d, 1H). |
| 5 | Methyl N-({8-[(2,6-difluorobenzyl)oxy]-2-methylimidazo[1,2-a]pyridin-3-yl}carbonyl)-2-methylalaninate $^{2)}$ 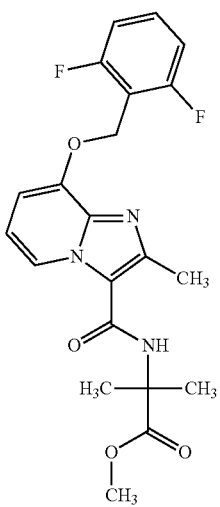 [SMILES: COC(=O)C(C)(C)NC(=O)c1c(C)nc2c(OCc3c(F)cccc3F)cccn12] (14% of theory; purity: 95%) | LC-MS (Method 5): $R_t$ = 0.90 min<br>MS (ESpos): m/z = 418.2 (M + H)$^+$ |

TABLE 1-continued

| Example | IUPAC-Name/Structure (Yield) | Analytical data |
|---|---|---|
| 6 | Methyl N-({8-[(2,6-difluorobenzyl)oxy]-2-methylimidazo[1,2-a]pyridin-3-yl}carbonyl)-D-alaninate [2)]<br>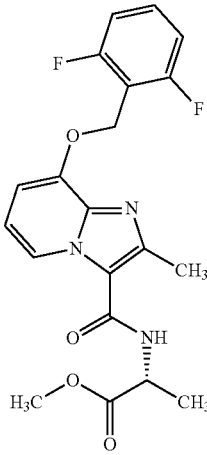<br>(45% of theory; purity: 86%) | LC-MS (Method 5): $R_t$ = 0.89 min<br>MS (ESpos): m/z = 404.1 (M + H)$^+$ |
| 7 | Methyl N-({8-[(2,6-difluorobenzyl)oxy]-2-methylimidazo[1,2-a]pyridin-3-yl}carbonyl)-beta-alaninate<br>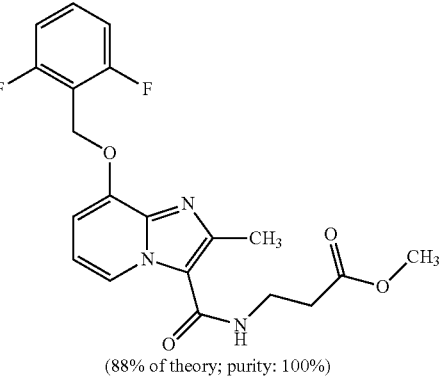<br>(88% of theory; purity: 100%) | LC-MS (Method 2): $R_t$ = 0.78 min<br>MS (ESpos): m/z = 404.2 (M + H)$^+$<br>$^1$H-NMR (400 MHz, DMSO-$d_6$):<br>δ = 2.48 (s, 3H), 2.63 (t, 2H), 3.50-3.58 (m, 2H), 3.62 (s, 3H), 5.30 (s, 2H), 6.94 (t, 1H), 7.02 (d, 1H), 7.23 (t, 2H), 7.54-7.64 (m, 1H), 7.94 (t, 1H), 8.62 (d, 1H). |
| 8 | rac-Methyl N-({8-[(2,6-difluorobenzyl)oxy]-2-methylimidazo[1,2-a]pyridin-3-yl}carbonyl)norleucinate<br>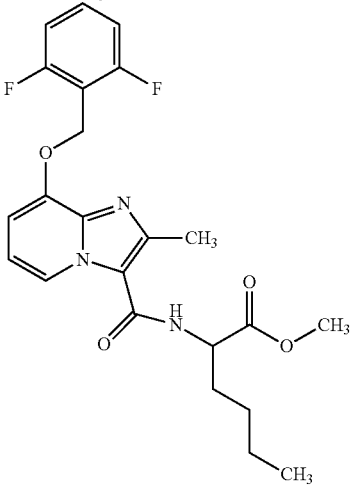 [SMILES: CCCCC(NC(=O)c1c(C)nc2c(OCc3c(F)cccc3F)cccn12)C(=O)OC]<br>(97% of theory; purity: 99%) | LC-MS (Method 1): $R_t$ = 1.15 min<br>MS (ESpos): m/z = 446.2 (M + H)$^+$<br>$^1$H-NMR (400 MHz, DMSO-$d_6$):<br>δ = 0.88 (t, 3H), 1.25-1.45 (m, 4H), 1.73-1.90 (m, 2H), 3.68 (s, 3H), 4.41-4.49 (m, 1H), 5.31 (s, 2H), 6.96 (t, 1H), 7.02 (d, 1H), 7.23 (t, 2H), 7.54-7.64 (m, 1H), 8.28 (d, 1H), 8.50 (d, 1H), [further signal hidden under DMSO peak]. |

TABLE 1-continued

| Example | IUPAC-Name/Structure (Yield) | Analytical data |
|---|---|---|
| 9 | rac-Methyl 2-[({8-[(2,6-difluorobenzyl)oxy]-2-methylimidazo[1,2-a]pyridin-3-yl}carbonyl)amino]-4,4,4-trifluorobutanoate<br>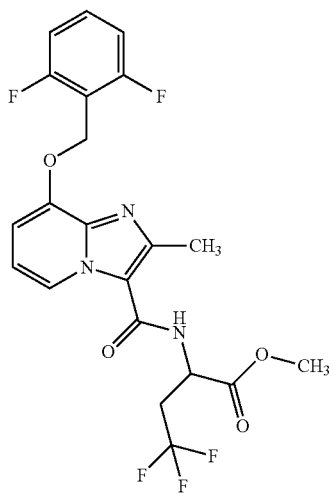 [SMILES: COC(=O)C(CC(F)(F)F)NC(=O)c1c(C)nc2c(OCc3c(F)cccc3F)cccn12]<br>(80% of theory) | LC-MS (Method 2): $R_t$ = 0.95 min<br>MS (ESpos): m/z = 472 (M + H)$^+$<br>$^1$H-NMR (400 MHz, DMSO-d$_6$): δ = 2.50 (s, 3H), 2.88-3.04 (m, 2H), 3.72 (s, 3H), 4.80-4.87 (m, 1H), 5.31 (s, 2H), 6.98 (t, 1H), 7.07 (d, 1H), 7.22 (t, 2H), 7.59 (quint, 1H), 8.49 (d, 1H), 8.58 (d, 1H). |
| 10 | rac-Methyl N-({8-[(2,6-difluorobenzyl)oxy]-2-methylimidazo[1,2-a]pyridin-3-yl}carbonyl)-5,5,5-trifluoronorvalinate<br>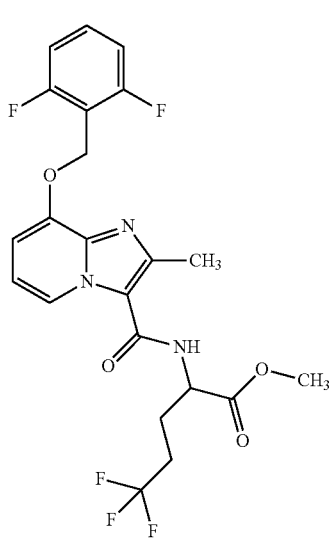 [SMILES: COC(=O)C(CCC(F)(F)F)NC(=O)c1c(C)nc2c(OCc3c(F)cccc3F)cccn12]<br>(91% of theory) | LC-MS (Method 3): $R_t$ = 2.05 min<br>MS (ESpos): m/z = 486 (M + H)$^+$<br>$^1$H-NMR (400 MHz, DMSO-d$_6$): δ = 1.97-2.18 (m, 2H), 2.30-2.54 (m, 2H), below this at 2.50 (s, 3H), 3.71 (s, 3H), 4.59-4.67 (m, 1H), 5.32 (s, 2H), 6.96 (t, 1H), 7.04 (d, 1H), 7.22 (t, 2H), 7.60 (quint, 1H), 8.34 (d, 1H), 8.55 (d, 1H). |

TABLE 1-continued

| Example | IUPAC-Name/Structure (Yield) | Analytical data |
|---|---|---|
| 11 | rac-Methyl N-({8-[(2,6-difluorobenzyl)oxy]-2-methylimidazo[1,2-a]pyridin-3-yl}carbonyl)-6,6,6-trifluoronorleucinate<br>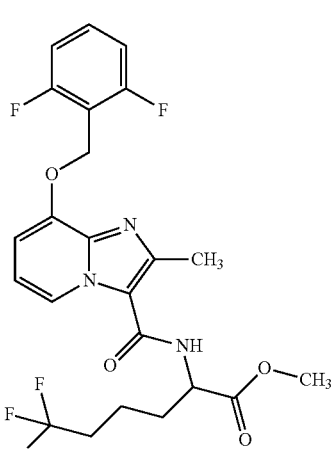<br>(95% of theory) | LC-MS (Method 2): $R_t$ = 1.04 min<br>MS (ESpos): m/z = 500 (M + H)$^+$<br>$^1$H-NMR (400 MHz, DMSO-d$_6$): δ = 1.59-1.69 (m, 2H), 1.80-2.01 (m, 2H), 2.20-2.43 (m, 2H), 2.50 (s, 3H), 3.70 (s, 3H), 4.49-4.57 (m, 1H), 5.31 (s, 2H), 6.94 (t, 1H), 7.03 (d, 1H), 7.22 (t, 2H), 7.60 (quint, 1H), 8.33 (d, 1H), 8.49 (d, 1H). |
| 12 | rac-Methyl N-({8-[(2,6-difluorobenzyl)oxy]-2,6-dimethylimidazo[1,2-a]pyridin-3-yl}carbonyl)-6,6,6-trifluoronorleucinate<br>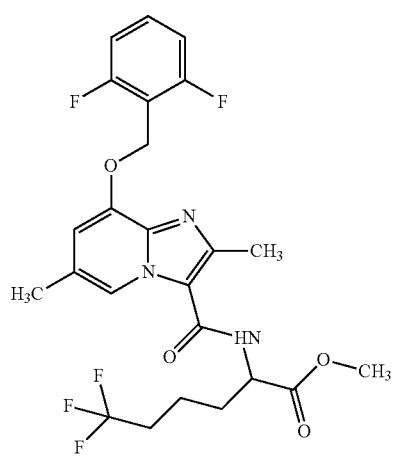<br>(64% of theory; purity: about 92%) | LC-MS (Method 2): $R_t$ = 1.03 min<br>MS (ESpos): m/z = 514 (M + H)$^+$<br>$^1$H-NMR (400 MHz, DMSO-d$_6$): δ = 1.58-1.69 (m, 2H), 1.78-2.01 (m, 2H), 2.20-2.43 (m, 5H), 2.50 (s, 3H), 3.70 (s, 3H), 4.48-4.56 (m, 1H), 5.30 (s, 2H), 6.92 (s, 1H), 7.22 (t, 2H), 7.60 (quint, 1H), 8.28-8.34 (m, 2H). |

TABLE 1-continued

| Example | IUPAC-Name/Structure (Yield) | Analytical data |
|---|---|---|
| 13 | rac-Methyl N-({6-chloro-8-[(2,6-difluorobenzyl)oxy]-2-methylimidazo[1,2-a]pyridin-3-yl}carbonyl)-6,6,6-trifluoronorleucinate 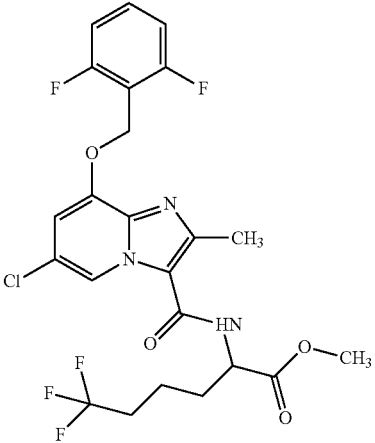 [SMILES: COC(=O)C(CCCC(F)(F)F)NC(=O)c1c(C)nc2c(OCc3c(F)cccc3F)cc(Cl)cn12] (78% of theory; purity: about 91%) | LC-MS (Method 2): $R_f$ = 1.23 min<br>MS (ESpos): m/z = 534 (M + H)$^+$<br>$^1$H-NMR (400 MHz, DMSO-d$_6$): δ = 1.58-1.69 (m, 2H), 1.78-2.01 (m, 2H), 2.19-2.43 (m, 2H), 2.50 (s, 3H), 3.70 (s, 3H), 4.48-4.57 (m, 1H), 5.34 (s, 2H), 7.19-7.28 (m, 3H), 7.61 (quint, 1H), 8.43 (d, 1H), 8.59 (s, 1H). |
| 14 | rac-Methyl N-({2,6-dimethyl-8-[(2,3,6-trifluorobenzyl)oxy]imidazo[1,2-a]pyridin-3-yl}carbonyl)-6,6,6-trifluoronorleucinate 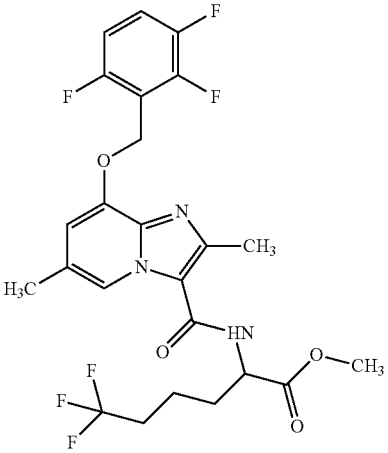 (69% of theory; purity about 92%) | LC-MS (Method 2): $R_f$ = 1.05 min<br>MS (ESpos): m/z = 532 (M + H)$^+$<br>$^1$H-NMR (400 MHz, DMSO-d$_6$):<br>δ = 1.58-1.69 (m, 2H), 1.79-2.01 (m, 2H), 2.20-2.43 (m, 5H), 2.50 (s, 3H), 3.70 (s, 3H), 4.48-4.55 (m, 1H), 5.34 (s, 2H), 6.93 (s, 1H), 7.25-7.7.33 (m, 1H), 7.61-7.72 (m, 1H), 8.28-8.36 (m, 2H). |
| 15 | Methyl 8-[({8-[(2,6-difluorobenzyl)oxy]-2-methylimidazo[1,2-a]pyridin-3-yl}carbonyl)amino]octanoate [1)] 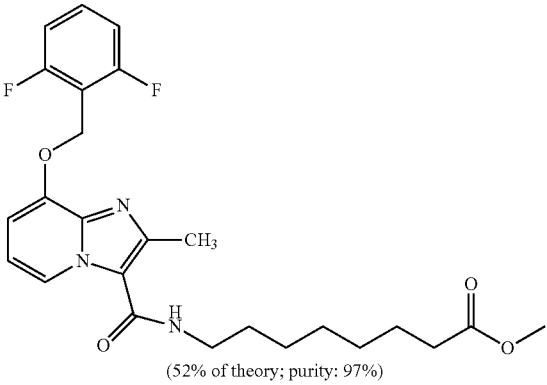 (52% of theory; purity: 97%) | LC-MS (Method 2): $R_f$ = 0.99 min<br>MS (ESpos): m/z = 474 (M + H)$^+$<br>$^1$H-NMR (400 MHz, DMSO-d$_6$):<br>δ = 1.19-1.40 (m, 6H), 1.43-1.60 (m, 4H), 2.29 (t, 2H), 3.25-3.32 (m, 2H), 3.58 (s, 3H), 5.30 (s, 2H), 6.91 (t, 1H), 6.99 (d, 1H), 7.22 (t, 2H), 7.60 (quint, 1H), 7.88 (t, 1H), 8.59 (d, 1H), [further signal hidden under solvent peak]. |

TABLE 1-continued

| Example | IUPAC-Name/Structure (Yield) | Analytical data |
|---|---|---|
| 16 | Methyl 8-[({8-[(2,6-difluorobenzyl)oxy]-2-methylimidazo[1,2-a]pyridin-3-yl}carbonyl)amino]octanoate [1]<br>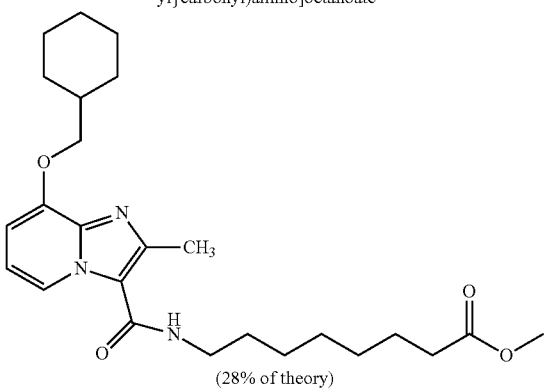<br>(28% of theory) | LC-MS (Method 2): $R_t$ = 1.04 min<br>MS (ESpos): m/z = 444 (M + H)$^+$<br>$^1$H-NMR (400 MHz, DMSO-$d_6$):<br>δ = 0.99-1.13 (m, 2H), 1.16-1.39 (m, 9H), 1.44-1.59 (m, 4H), 1.63-1.78 (m, 3H), 1.81-1.91 (m, 3H), 2.29 (t, 2H), 3.25-3.32 (m, 2H), 3.58 (s, 3H), 3.94 (d, 2H), 6.77 (d, 1H), 6.85 (t, 1H), 7.84 (t, 1H), 8.53 (d, 1H), [further signal hidden under solvent peak]. |

[1] Preparation of the amine according to Soler, Francoise; Poujade, Christele; Evers, Michel; Carry, Jean-Christophe; Henin, Yvette; et al.; *Journal of Medicinal Chemistry*, 1996, vol. 39, 1069-1083)

Example 17 rac-Methyl 3-[({8-[(2,6-difluorobenzyl)oxy]-2-methylimidazo[1,2-a]pyridin-3-yl}carbonyl)-amino]-4,4,4-trifluorobutanoate

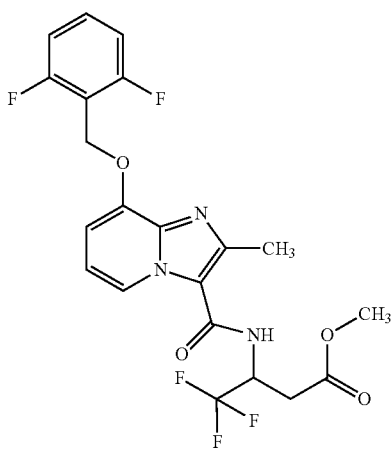 [SMILES: COC(=O)CC(NC(=O)c1c(C)nc2c(OCc3c(F)cccc3F)cccn12)C(F)(F)F]

750 mg of 8-[(2,6-difluorobenzyl)oxy]-2-methylimidazo[1,2-a]pyridine-3-carboxylic acid Example 3A (2.36 mmol, 1 equivalent) were initially charged in 15 ml of DMF, and 2.24 g of N-[(dimethylamino)(3H-[1,2,3]triazolo[4,5-b]pyridin-3-yloxy)methylidene]-N-methylmethanaminium hexafluorophosphate (HATU, 5.89 mmol, 2.5 equivalents) and 1.03 ml of N,N-diisopropylethylamine (0.76 g, 5.89 mmol, 2.5 equivalents) were added. The mixture was stirred at 60° C. for 20 min, 0.98 g of methyl 3-amino-4,4,4-trifluorobutanoate hydrochloride (Example 22A, 4.71 mmol, 2 equivalents) was added and the mixture was stirred at 60° C. overnight. The mixture was then added to 120 ml of water and stirred at RT for 30 min. The precipitated solid was filtered off, washed with 6 ml of diethyl ether and dried under reduced pressure. The residue was then concentrated on a silica gel column (mobile phases: dichloromethane/ethyl acetate 10:1). This gave 0.32 g (29% of theory) of the title compound.

LC-MS (Method 2): $R_t$=0.98 min
MS (ESpos): m/z=472.2 (M+H)$^+$
$^1$H-NMR (400 MHz, DMSO-$d_6$): δ=2.46 (s, 3H), 2.85-3.03 (m, 2H), 3.64 (s, 3H), 5.16-5.27 (m, 1H), 5.32 (s, 2H), 6.99 (t, 1H), 7.05 (d, 1H), 7.19-7.27 (m, 2H), 7.54-7.64 (m, 1H), 8.45 (d, 1H), 8.53 (d, 1H).

Example 18 ent-Methyl N-({8-[(2,6-difluorobenzyl)oxy]-2-methylimidazo[1,2-a]pyridin-3-yl}carbonyl)-norleucinate (Enantiomer A)

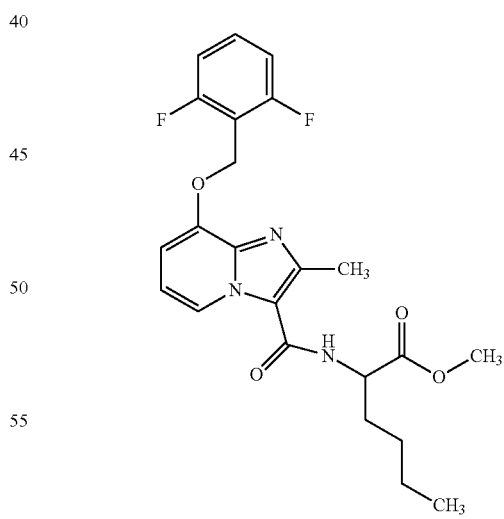

Example 8 (2 g) was separated into the enantiomers by preparative separation on a chiral phase [column: Daicel Chiralpak AD-H, 5 μm, 250×20 mm, mobile phase: ethanol, flow rate 15 ml/min, 45° C., detection: 220 nm].

Yield: 0.96 g (97% pure, 99% ee)

Enantiomer A: $R_t$=19.12 min [Chiralpak AD-H, 5 μm, 250×4.6 mm, mobile phase: ethanol; flow rate 1.0 ml/min; 45° C.; detection: 220 nm]. .

Example 19 ent-Methyl N-({8-[(2,6-difluorobenzyl)oxy]-2-methylimidazo[1,2-a]pyridin-3-yl}carbonyl)-norleucinate (Enantiomer B)

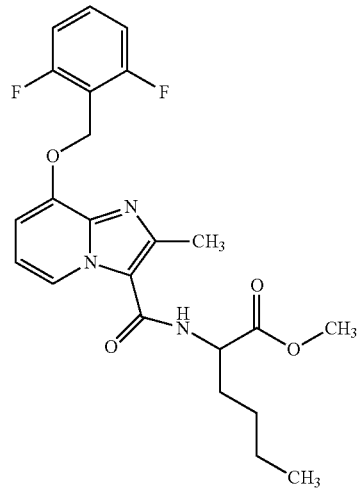 [SMILES: CCCCC(NC(=O)c1c(C)nc2c(OCc3c(F)cccc3F)cccn12)C(=O)OC]

Example 8 (2 g) was separated into the enantiomers by preparative separation on a chiral phase [column: Daicel Chiralpak AD-H, 5 μm, 250×20 mm, mobile phase: ethanol, flow rate 15 ml/min, 45° C., detection: 220 nm].

Yield: 1.06 g (97% pure, 99% ee).

Enantiomer B: $R_t$=40.97 min [Chiralpak AD-H, 5 μm, 250×4.6 mm, mobile phase: ethanol; flow rate 1.0 ml/min; 45° C.; detection: 220 nm].

Example 20

8-({[8-(Cyclohexylmethoxy)-2-methylimidazo[1,2-a]pyridin-3-yl]carbonyl}amino)octanoic acid

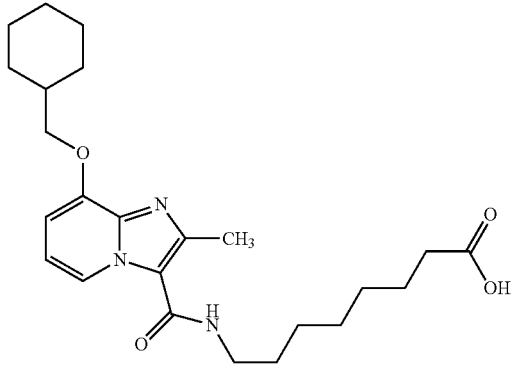 [SMILES: Cc1nc2c(OCC3CCCCC3)cccn2c1C(=O)NCCCCCCCC(=O)O]

67 mg of methyl 8-({[8-(cyclohexylmethoxy)-2-methylimidazo[1,2-a]pyridin-3-yl]carbonyl}-amino)octanoate Example 16 (0.15 mmol, 1 equivalent) were dissolved in 2.5 ml of THF, and 0.3 ml of 1 M lithium hydroxide solution in water (0.3 mmol, 2 equivalents) was added. The mixture was stirred at RT overnight and then acidified with 1 M aq. hydrochloric acid and concentrated. The residue was dissolved in methanol/acetonitrile and purified by preparative HPLC (RP18 column, mobile phase: acetonitrile/water gradient with addition of 0.1% formic acid). this gave 22 mg (34% of theory; purity: 100%) of the title compound.

LC-MS (Method 2): $R_t$=0.94 min
MS (ESpos): m/z=430.2 (M+H)$^+$ $^1$H-NMR (400 MHz, DMSO-d$_6$): δ=1.02-1.15 (m, 2H), 1.21-1.39 (m, 8H), 1.46-1.59 (m, 4H), 1.61-1.76 (m, 3H), 1.77-1.91 (m, 3H), 2.20 (t, 2H), 2.53 (s, 3H), 3.95 (d, 2H), 6.76 (d, 1H), 6.85 (t, 1H), 7.83 (t, 1H), 8.52 (d, 1H), 11.94 (s, 1H), [further signals hidden under solvent peaks].

Example 21

8-[({8-[(2,6-Difluorobenzyl)oxy]-2-methylimidazo[1,2-a]pyridin-3-yl}carbonyl)amino]octanoic acid

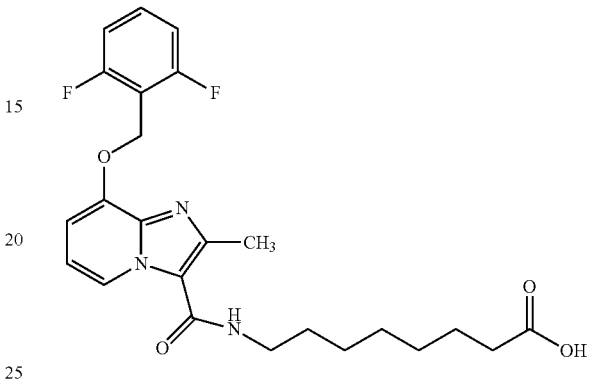

50 mg of methyl 8-[({8-[(2,6-difluorobenzyl)oxy]-2-methylimidazo[1,2-a]pyridin-3-yl}carbonyl)-amino]octanoate Example 15 (0.11 mmol, 1 equivalent) were reacted with 0.5 ml of 1 M lithium hydroxide solution in water (0.53 mmol, 5 equivalents) analogously to Example 20 and worked up. This gave 25 mg (47% of theory; purity: 92%) of the title compound.

LC-MS (Method 2): $R_t$=0.87 min
MS (ESpos): m/z=460.1 (M+H)$^+$ $^1$H-NMR (400 MHz, DMSO-d$_6$): δ=1.24-1.38 (m, 6H), 1.45-1.60 (m, 4H), 2.20 (t, 2H), 5.30 (s, 2H), 6.92 (t, 1H), 6.99 (d, 1H), 7.23 (t, 2H), 7.53-7.63 (m, 1H), 7.86 (t, 1H), 8.59 (d, 1H), 11.89-12.00 (m, 1H), [further signals hidden under solvent peaks].

Example 22

6-({[8-(Cyclohexylmethoxy)-2-methylimidazo[1,2-a]pyridin-3-yl]carbonyl}amino)hexanoic acid

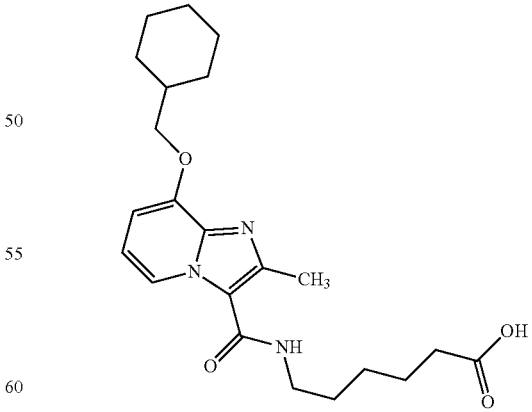

18 mg of methyl 6-aminohexanoate hydrochloride (0.1 mmol, 1.0 equivalent) were initially charged, and 29 mg of 8-(cyclohexylmethoxy)-2-methylimidazo[1,2-a]pyridine-3-carboxylic acid Example 6A (0.1 mmol, 1 equivalent) in 0.3 ml of DMSO, 41.7 mg of (benzotriazol-1-yloxy)bisdimethylaminomethyliumfluoroborate (TBTU, 0.13 mmol, 1.3 equivalents) in 0.3 ml of DMSO and 26 mg of N,N-diisopropylethylamine (0.2 mmol, 2 equivalents) were added in succession. The mixture was shaken at RT overnight, 0.4 ml of 2 N sodium hydroxide solution was added and the mixture was once more shaken at RT overnight. The solvent was then evaporated and the mixture was purified by preparative HPLC (Method 10). This gave 11 mg (26% of theory; purity: 100%) of the title compound.

LC-MS (Method 5): $R_t$=0.90 min

MS (ESpos): m/z=402.8 (M+H)$^+$

Example 23

N-({8-[(2,6-Difluorobenzyl)oxy]-2-methylimidazo[1,2-a]pyridin-3-yl}carbonyl)norleucine hydrochloride

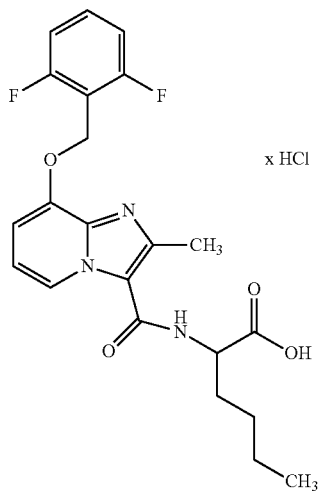 [SMILES: CCCCC(NC(=O)c1c(C)nc2c(OCc3c(F)cccc3F)cccn12)C(=O)O]

890 mg of methyl N-({8-[(2,6-difluorobenzyl)oxy]-2-methylimidazo[1,2-a]pyridin-3-yl}carbonyl)-D-norleucinate Example 19 (2 mmol, 1 equivalent) were dissolved in 16 ml of THF/methanol (1:1), 10 ml of 1 N aqueous lithium hydroxide solution (10 mmol, 5 equivalents) were added and the mixture was stirred at 45° C. for 2 h. With ice cooling, the mixture was then adjusted to pH 5-6 using 6 N aqueous hydrochloric acid, and the organic solvent was removed under reduced pressure. A little water was added to the residue, and the mixture was extracted repeatedly with dichloromethane/methanol=100:5. The combined organic phases were dried over magnesium sulphate, filtered and concentrated. The residue obtained was dried under high vacuum. This gave 844 mg (95% of theory; purity: 98%) of the title compound.

LC-MS (Method 2): $R_t$=0.89 min

MS (ESpos): m/z=432.3 (M+H)$^+$ $^1$H-NMR (400 MHz, DMSO-d$_6$): δ=0.89 (t, 3H), 1.26-1.45 (m, 4H), 1.72-1.92 (m, 2H), 2.58 (s, 3H), 4.38-4.46 (m, 1H), 5.39 (s, 2H), 7.25 (t, 3H), 7.31-7.45 (br. s, 1H), 7.55-7.65 (m, 1H), 8.48 (br. s, 1H), 8.60 (d, 1H), 12.79 (br. s, 1H).

Example 24

Methyl trans-4-{[({8-[(2,6-difluorobenzyl)oxy]-2,6-dimethylimidazo[1,2-a]pyridin-3-yl}carbonyl)amino]methyl}cyclohexanecarboxylate

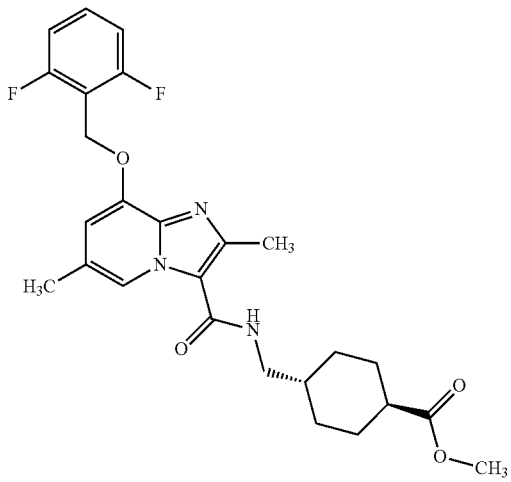 [SMILES: COC(=O)[C@H]1CC[C@H](CNC(=O)c2c(C)nc3c(OCc4c(F)cccc4F)cc(C)cn23)CC1]

Under argon, 125 mg of 8-[(2,6-difluorobenzyl)oxy]-2,6-dimethylimidazo[1,2-a]pyridine-3-carboxylic acid Example 19A (0.38 mmol, 1 equivalent) were suspended in 2.4 ml of DMF, and 181 mg of (benzotriazol-1-yloxy)bisdimethylaminomethyliumfluoroborate (TBTU, 0.56 mmol, 1.5 equivalents), 0.21 ml of 4-methylmorpholine (190 mg, 1.88 mmol, 5 equivalents) and 94 mg of methyl trans-4-(aminomethyl)cyclohexanecarboxylate hydrochloride (0.45 mmol, 1.2 equivalents) were added in succession. The mixture was stirred at RT overnight, diluted (water/THF) and purified directly by preparative HPLC (RP18 column, mobile phase: acetonitrile/water gradient with addition of 0.1% TFA). The fractions, concentrated on a rotary evaporator, were taken up in dichloromethane and washed twice with saturated aqueous sodium bicarbonate solution. The combined aqueous phases were re-extracted twice with dichloromethane. The combined organic phases were dried over sodium sulphate, filtered and concentrated on a rotary evaporator. This gave 144 mg (75% of theory; purity: 95%) of the title compound.

LC-MS (Method 2): $R_t$=0.92 min

MS (ESpos): m/z=486.3 (M+H)$^+$ $^1$H-NMR (400 MHz, DMSO-d$_6$): δ=0.92-1.09 (m, 2H), 1.20-1.40 (m, 2H), 1.47-1.61 (m, 1H), 1.64-1.97 (m, 5H), 2.31 (s, 3H), 3.18 (t, 2H), 3.58 (s, 3H), 5.28 (s, 2H), 6.89 (s, 1H), 7.19-7.28 (m, 2H), 7.53-7.63 (m, 1H), 8.34 (t, 1H), 8.41 (s, 1H), [further signal hidden under DMSO peak].

Example 25 trans-4-{[({8-[(2,6-Difluorobenzyl)oxy]-2,6-dimethylimidazo[1,2-a]pyridin-3-yl}carbonyl)amino]methyl}cyclohexanecarboxylic acid

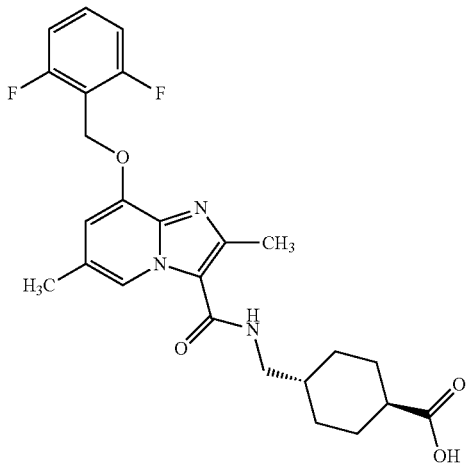 [SMILES: Cc1cc(OCc2c(F)cccc2F)c2nc(C)c(C(=O)NC[C@H]3CC[C@H](C(=O)O)CC3)n2c1]

131 mg of methyl trans-4-{[({8-[(2,6-difluorobenzyl)oxy]-2,6-dimethylimidazo[1,2-a]pyridin-3-yl}carbonyl)amino]methyl}cyclohexanecarboxylate Example 24 (0.26 mmol, 1 equivalent) were dissolved in 5.5 ml of THF/methanol, (5:1), 1.28 ml of 1 N aqueous lithium hydroxide solution (1.28 mmol, 5 equivalents) were added and the mixture was stirred at RT for 4 h. With ice cooling, the mixture was adjusted to pH 4 using 1 N aqueous hydrochloric acid, and the organic solvent was evaporated. The residue obtained was extracted three times with dichloromethane. The combined organic phases were washed once with water, dried over magnesium sulphate, filtered and concentrated. Three times, the residue was taken up in dichloromethane, in each case mixed with 1 ml of formic acid and concentrated again. The crude product was purified by thick-layer chromatography (mobile phase: dichloromethane/isopropanol=10/1). This gave 37 mg (30% of theory) of the title compound.

LC-MS (Method 2): $R_t$=0.79 min

MS (ESpos): m/z=472.3 (M+H)$^+$ $^1$H-NMR (400 MHz, DMSO-$d_6$): δ=0.92-1.09 (m, 2H), 1.22-1.38 (m, 2H), 1.46-1.60 (m, 1H), 1.78-1.96 (m, 4H), 2.10-2.20 (m, 1H), 2.31 (s, 3H), 3.18 (t, 2H), 5.28 (s, 2H), 6.90 (s, 1H), 7.19-7.28 (m, 2H), 7.54-7.63 (m, 1H), 8.34 (t, 1H), 8.41 (s, 1H), [further signal hidden under DMSO peak].

B. Assessment of the Pharmacological Activity

The following abbreviations are used:
ATP adenosine triphosphate
Brij35 polyoxyethylene (23) lauryl ether
BSA bovine serum albumin
DTT dithiothreitol
TEA triethanolamine The pharmacological effect of the compounds according to the invention can be shown in the following assays:

B-1. Measurement of sGC Enzyme Activity by Detection of PPi

Soluble guanylate cyclase (sGC) converts on stimulation GTP into cGMP and pyrophosphate (PPi). PPi is detected with the aid of the method described in WO 2008/061626. The signal produced in the test increases as the reaction progresses and serves as a measure of the sGC enzyme activity. With the aid of a PPi reference curve, the enzyme can be characterized in a known manner, for example with respect to conversion rate, stimulability or Michaelis constant.

Practice of the Test

To carry out the test, 29 μl of enzyme solution (0-10 nM soluble guanylate cyclase (prepared according to Honicka et al., Journal of Molecular Medicine 77 (1999) 14-23) in 50 mM TEA, 2 mM magnesium chloride, 0.1% BSA (fractionV), 0.005% Brij 35, pH 7.5) were initially introduced into the microplate, and 1 μl of the stimulator solution (0-10 μM 3-morpholinosydnonimine, SIN-1, Merck in DMSO) were added. The mixture was incubated at RT for 10 min. 20 μl of detection mix (1.2 nM Firefly Luciferase (*Photinus pyralis* Luziferase, Promega), 29 μM dehydroluciferin (prepared according to Bitler & McElroy, Arch. Biochem. Biophys. 72 (1957) 358), 122 μM luciferin (Promega), 153 μM ATP (Sigma) and 0.4 mM DTT (Sigma) in 50 mM TEA, 2 mM magnesium chloride, 0.1% BSA (fraction V), 0.005% Brij 35, pH 7.5) were added. The enzyme reaction was started by addion of 20 μl of substrate solution (1.25 mM guanosine 5'-triphosphate (Sigma) in 50 mM TEA, 2 mM magnesium chloride, 0.1% BSA (fraction V), 0.005% Brij 35, pH 7.5) and measured continuously in a luminometer.

B-2. Action on Recombinant Guanylate Cyclase Reporter Cell Line

The cellular action of the compounds according to the invention is determined on a recombinant guanylate cyclase reporter cell line, as described in F. Wunder et al., *Anal. Biochem.* 339, 104-112 (2005).

Representative MEC values (MEC=minimal effective concentration) for the compounds according to the invention are shown in the following table:

TABLE A

| Example | MEC [μM] |
|---|---|
| 1 | 0.3 |
| 2 | 0.3 |
| 3 | 0.3 |
| 4 | 1.0 |
| 5 | 0.3 |
| 6 | 3.0 |
| 7 | 1.0 |
| 8 | 1.0 |
| 9 | 3.0 |
| 10 | 1.0 |
| 11 | 0.3 |
| 12 | 0.3 |
| 13 | 0.3 |
| 14 | 0.3 |
| 15 | 1.0 |
| 16 | 0.3 |
| 17 | 1.0 |
| 18 | 0.3 |
| 19 | 1.0 |
| 20 | 0.065 |
| 21 | 0.1 |
| 22 | 0.3 |
| 23 | 2.0 |
| 24 | 0.1 |
| 25 | 1.0 |

B-3. Vessel-Relaxing Action In Vitro

Rabbits are stunned with a blow on the back of the neck and exsanguinated. The aorta is removed, freed from adhering tissue, separated into rings with a width of 1.5 mm, and placed individually, with preloading, in 5-ml organ baths with carbogen-gassed Krebs-Henseleit solution at 37° C. with the following composition (mM in each case): sodium chloride: 119; potassium chloride: 4.8; calcium chloride dihydrate: 1; magnesium sulphate heptahydrate: 1.4; potassium dihydrogen phosphate: 1.2; sodium hydrogen carbonate: 25; glucose: 10. The contraction force is recorded with Statham UC2 cells, amplified and digitized via an A/D converter (DAS-1802 HC, Keithley Instruments Munich) and recorded in parallel on a continuous-line recorder. To produce contraction, phenylephrine is added to the bath cumulatively in increasing concentration. After several control cycles, the test substance is added in increasing dosage in each subsequent pass and the level of contraction is compared with the level of contraction reached in the immediately preceding pass. This is used for calculating the concentration that is required to reduce the level of the control value by 50% ($IC_{50}$ value). The standard application volume is 5 µl, and the proportion of DMSO in the bath solution corresponds to 0.1%.

B-4. Measurement of Blood Pressure on Anaesthetized Rats

Male Wistar rats having a body weight of 300-350 g are anaesthetized with thiopental (100 mg/kg i.p.). After tracheotomy, a catheter for measuring the blood pressure is introduced into the femoral artery. The substances to be tested are administered as solutions either orally by gavage or intravenously via the femoral vein (Stasch et al. Br. J. Pharmacol. 2002; 135: 344-355).

B-5. Radiotelemetric Blood Pressure Measurement on Awake, Spontaneously Hypertensive Rats The blood pressure measurement on awake rats described below uses a commercially available telemetry system from the company DATA SCIENCES INTERNATIONAL DSI, USA.

The system consists of 3 main components:
implantable transmitter (Physiotel® Telemetry Transmitter)
receiver (Physiotel® Receiver), which are connected via a multiplexer (DSI Data ExchangeMatrix) to a
data acquisition computer.

The telemetry system provides continuous acquisition of blood pressure, heart rate and body movement on awake animals in their usual living space.

Animal Material

The investigations are carried out on adult female, spontaneously hypertensive rats (SHR Okamoto) with a body weight of >200 g. SHR/NCrl from Okamoto Kyoto School of Medicine, 1963 were crossed from male Wistar Kyoto rats with greatly increased blood pressure and females with slightly raised blood pressure and were delivered in F13 to the U.S. National Institutes of Health.

After transmitter implantation, the experimental animals are kept individually in Makrolon cages, type 3. They have free access to standard feed and water.

The day-night rhythm in the testing laboratory is alternated by the room lighting at 06:00 hours in the morning and at 19:00 hours in the evening.

Transmitter Implantation

The TA11-C40 telemetry transmitters used are implanted surgically in the experimental animals under aseptic conditions at least 14 days before the first test. The animals provided with this instrumentation can be used again after the wound has healed and the implant has become incorporated.

For implantation, the fasting animals are anaesthetized with pentobarbital (Nembutal, Sanofi: 50 mg/kg i.p.) and are shaved and disinfected on a wide area of the abdomen. After opening the abdominal cavity along the linea alba, the liquid-filled measuring catheter of the system is inserted above the bifurcation in the cranial direction into the aorta descendens and secured with tissue adhesive (VetBonD™, 3M). The transmitter housing is fixed intraperitoneally on the abdominal wall musculature and the wound is closed layer by layer.

Postoperatively, an antibiotic is administered to prevent infection (Tardomyocel COMP Bayer 1 ml/kg s.c.)

Substances and Solutions

Unless described otherwise, the test substances are in each case administered orally by stomach tube to a group of animals (n=6). Corresponding to an application volume of 5 ml/kg body weight, the test substances are dissolved in suitable solvent mixtures or suspended in 0.5% Tylose.

A group of animals treated with solvents is used as control.

Test Procedure

The present telemetry measuring device is configured for 24 animals. Each test is recorded under a test number (Vtest year month day).

The instrumented rats living in the unit are each assigned their own receiving antenna (1010 Receiver, DSI).

The implanted transmitters can be activated from outside by an in-built magnetic switch. They are switched to transmission at the start of the tests. The signals emitted can be recorded online by a data acquisition system (Dataquest™ A.R.T. for WINDOWS, DSI) and processed appropriately. The data are saved in each case to a folder opened for this, which bears the test number.

In the standard procedure, the following are measured, in each case for 10 seconds:
systolic blood pressure (SBP)
diastolic blood pressure (DBP)
mean arterial pressure (MAP)
heart rate (HR)
activity (ACT).

Recording of the measured values is repeated at 5-minute intervals under computer control. The source data recorded as absolute value are corrected in the diagram with the currently measured barometric pressure (Ambient Pressure Reference Monitor; APR-1) and saved in individual data. Further technical details can be found in the extensive documentation of the manufacturer (DSI).

Unless described otherwise, the test substances are administered on the test day at 09.00 hours. Following application, the parameters described above are measured for 24 hours.

Evaluation

After the end of the test, the individual data recorded are sorted with the analysis software (DATAQUEST™ A.R.T.™ ANALYSIS). The 2 hours before application are taken as the blank value here, so that the selected data set comprises the period from 07:00 hours on the test day to 09:00 hours on the next day.

The data are smoothed for a pre-settable time by mean value determination (15-minute average) and transferred as text file to a storage medium. The pre-sorted and compressed measured values are transferred to Excel templates and presented as tables. The data recorded are saved per test day in a specific folder, which bears the test number. Results and test protocols are filed in folders, sorted in paper form by numbers.

Literature

Klaus Witte, Kai Hu, Johanna Swiatek, Claudia Müssig, Georg Ertl and Bjorn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured with Radio-Telemetry. Physiology & Behavior 55(4): 783-787, 1994.

71

C. Exemplary Embodiments of Pharmaceutical Compositions

The compounds according to the invention can be converted into pharmaceutical preparations in the following ways:

Tablet:

Composition:

100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:

The mixture of compound according to the invention, lactose and starch is granulated with a 5% strength solution (m/m) of the PVP in water. The granules are dried and then mixed with the magnesium stearate for 5 minutes. This mixture is compressed in a conventional tablet press (see above for format of the tablet). A guideline compressive force for the compression is 15 kN.

Suspension which can be Administered Orally:

Composition:

1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:

The Rhodigel is suspended in ethanol, and the compound according to the invention is added to the suspension. The water is added while stirring. The mixture is stirred for about 6 h until the swelling of the Rhodigel is complete.

Solution which can be Administered Orally:

Composition:

500 mg of the compound according to the invention, 2.5 g of polysorbate and 97 g of polyethylene glycol 400.20 g of oral solution correspond to a single dose of 100 mg of the compound according to the invention.

Production:

The compound according to the invention is suspended in the mixture of polyethylene glycol and polysorbate with stirring. The stirring process is continued until the compound according to the invention has completely dissolved.

i.v. Solution:

The compound according to the invention is dissolved in a concentration below the saturation solubility in a physiologically tolerated solvent (e.g. isotonic saline, 5% glucose solution and/or 30% PEG 400 solution). The solution obtained is sterilized by filtration and used to fill sterile and pyrogen-free injection containers.

72

The invention claimed is:
1. A compound of formula (I)

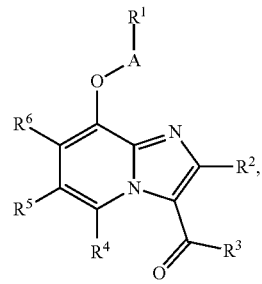

in which

A represents $CH_2$, $CD_2$ or $CH(CH_3)$, $R^1$ represents $(C_4-C_6)$-alkyl, $(C_3-C_7)$-cycloalkyl or phenyl,
where $(C_4-C_6)$-alkyl may be substituted up to six times by fluorine,
where $(C_3-C_7)$-cycloalkyl may be substituted by 1 to 4 substituents independently of one another selected from the group consisting of fluorine, trifluoromethyl and $(C_1-C_4)$-alkyl,
and
where phenyl may be substituted by 1 to 4 substituents independently of one another selected from the group consisting of halogen, cyano, monofluoromethyl, difluoromethyl, trifluoromethyl, $(C_1-C_4)$-alkyl, $(C_1-C_4)$-alkoxy, difluoromethoxy and trifluoromethoxy, $R^2$ represents hydrogen, $(C_1-C_4)$-alkyl, cyclopropyl, monofluoromethyl, difluoromethyl or trifluoromethyl, $R^3$ represents a group of the formula

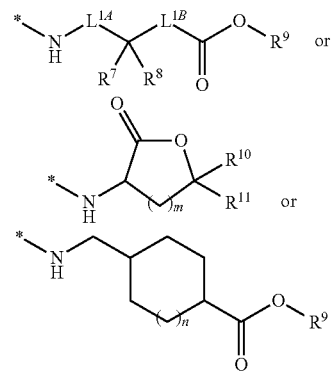

where
* represents the point of attachment to the carbonyl group, $L^{1A}$ represents a bond or $(C_1-C_4)$-alkanediyl,
where $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy, $L^{1B}$ represents a bond or $(C_1-C_4)$-alkanediyl,
where $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy, R⁷ represents hydrogen, $(C_1-C_6)$-alkyl, $(C_2-C_6)$-alkenyl, $(C_2-C_6)$-alkynyl, $(C_3-C_7)$-cycloalkyl, 5- or 6-membered heteroaryl or phenyl,
  where $(C_1-C_6)$-alkyl may be substituted by 1 to 3 substituents independently of one another selected from the group consisting of fluorine, trifluoromethyl, difluoromethoxy, trifluoromethoxy, hydroxy, $(C_1-C_4)$-alkoxy, phenyl, phenoxy and benzyloxy,
    where phenyl, phenoxy and benzyloxy for their part may be substituted by 1 or 2 halogen substituents,
  where $(C_3-C_7)$-cycloalkyl may be substituted by 1 or 2 substituents independently of one another selected from the group consisting of fluorine, trifluoromethyl, $(C_1-C_4)$-alkyl and $(C_1-C_4)$-alkoxy,
  and
  where phenyl and 5- or 6-membered heteroaryl may be substituted by 1 to 3 substituents independently of one another selected from the group consisting of halogen, cyano, trifluoromethyl, $(C_1-C_4)$-alkyl, $(C_1-C_4)$— alkoxy and $(C_1-C_4)$-alkylsulphonyl,
R⁸ represents hydrogen or $(C_1-C_4)$-alkyl,
or
R⁷ and R⁸ together with the carbon atom to which they are attached form a 3- to 7-membered carbocycle or a 4- to 7-membered heterocycle,
  where the 3- to 7-membered carbocycle and the 4- to 7-membered heterocycle may be substituted by 1 to 3 substituents independently of one another selected from the group consisting of fluorine and $(C_1-C_4)$-alkyl,
R⁹ represents hydrogen or $(C_1-C_6)$-alkyl,
R¹⁰ represents hydrogen or $(C_1-C_4)$-alkyl,
R¹¹ represents hydrogen or $(C_1-C_4)$-alkyl,
m represents 1, 2 or 3,
n represents 0, 1 or 2,
R⁴ represents hydrogen,
R⁵ represents hydrogen, halogen, cyano, difluoromethyl, trifluoromethyl, $(C_1-C_4)$-alkyl, $(C_3-C_7)$-cycloalkyl, $(C_2-C_4)$-alkynyl, difluoromethoxy, trifluoromethoxy or $(C_1-C_4)$-alkoxy,
R⁶ represents hydrogen or halogen,
and its N-oxides, salts, solvates, salts of the N-oxides and solvates of the N-oxides and salts.

2. The compound of claim 1 in which
A represents $CH_2$,
R¹ represents $(C_4-C_6)$-cycloalkyl or phenyl,
  where phenyl may be substituted by 1 to 3 substituents selected from the group consisting of fluorine and chlorine,
R² represents methyl, ethyl or trifluoromethyl,
R³ represents a group of the formula

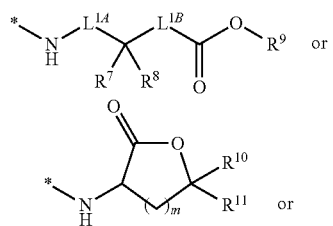

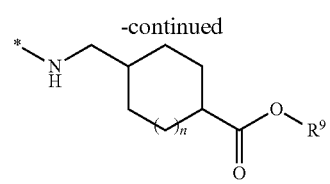

where
* represents the point of attachment to the carbonyl group,
$L^{1A}$ represents a bond or $(C_1-C_4)$-alkanediyl,
  where $(C_1-C_4)$-alkanediyl may be substituted by 1 to 3 substituents independently of one another selected from the group consisting of fluorine, trifluoromethyl, hydroxyl and $(C_1-C_4)$-alkyl,
$L^{1B}$ represents a bond or $(C_1-C_4)$-alkanediyl,
  where $(C_1-C_4)$-alkanediyl may be substituted by 1 to 3 substituents independently of one another selected from the group consisting of fluorine, trifluoromethyl, hydroxy and $(C_1-C_4)$-alkyl,
R⁷ represents hydrogen, trifluoromethyl, $(C_1-C_6)$-alkyl, 5- or 6-membered heteroaryl or phenyl,
  where $(C_1-C_6)$-alkyl may be substituted by 1 to 2 substituents independently of one another selected from the group consisting of fluorine, trifluoromethyl and phenyl,
    where phenyl may be substituted by 1 or 2 substituents selected from the group consisting of fluorine and chlorine,
  and
  where phenyl and 5- or 6-membered heteroaryl may be substituted by 1 to 2 substituents independently of one another selected from the group consisting of fluorine, chlorine and cyano,
R⁸ represents hydrogen, methyl or ethyl,
R⁹ represents hydrogen, methyl or ethyl,
R¹⁰ represents hydrogen or methyl,
R¹¹ represents hydrogen or methyl,
m represents 1, 2 or 3,
n represents 0, 1 or 2,
R⁴ represents hydrogen,
R⁵ represents hydrogen, fluorine, chlorine, difluoromethyl, trifluoromethyl methyl or ethyl,
R⁶ represents hydrogen,
and its N-oxides, salts, solvates, salts of the N-oxides and solvates of the N-oxides and salts.

3. The compound of claim 1 in which
A represents $CH_2$,
R¹ represents a phenyl group of the formula

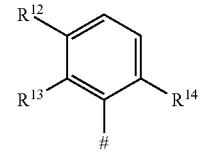

where
# represents the point of attachment to A,
and
R¹², R¹³ and R¹⁴ independently of one another represent hydrogen, fluorine or chlorine,
with the proviso that at least two of the radicals R¹², R¹³, R¹⁴ are different from hydrogen, $R^2$ represents methyl, $R^3$ represents a group of the formula

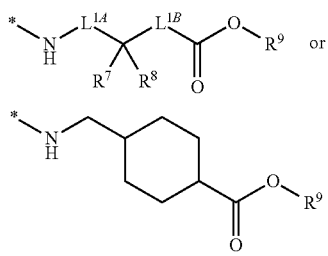

where

* represents the point of attachment to the carbonyl group, $L^{1A}$ represents a bond or $(C_1$-$C_4)$-alkanediyl, $L^{1B}$ represents a bond or $(C_1$-$C_4)$-alkanediyl, $R^7$ represents hydrogen, trifluoromethyl, $(C_1$-$C_6)$-alkyl or phenyl, where $(C_1$-$C_6)$-alkyl may be substituted by 1 to 2 substituents selected from the group consisting of fluorine and trifluoromethyl, where phenyl may be substituted by 1 to 2 substituents selected from the group consisting of fluorine and chlorine, $R^8$ represents hydrogen or methyl, $R^9$ represents hydrogen, methyl or ethyl, $R^4$ represents hydrogen, $R^5$ represents hydrogen, fluorine, chlorine or methyl, $R^6$ represents hydrogen, and its N-oxides, salts, solvates, salts of the N-oxides and solvates of the N-oxides and salts.

4. A process for preparing the compound of claim 1, comprising:

[A] reacting a compound of formula (II)

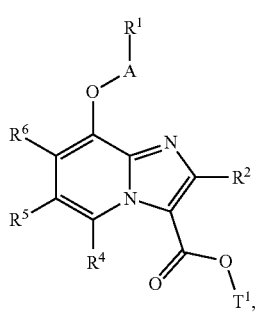

in which A, $R^1$, $R^2$, $R^4$, $R^5$ and $R^6$ each have the meanings given in claim 1 and $T^1$ represents $(C_1$-$C_4)$-alkyl or benzyl, in an inert solvent in the presence of a suitable base or acid to give a carboxylic acid of formula (III)

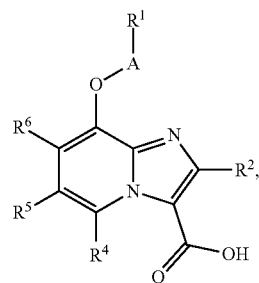

in which A, $R^1$, $R^2$, $R^4$, $R^5$ and $R^6$ each have the meanings given above, reacting the compound of formula (III-A) in an inert solvent under amide coupling conditions with an amine of the formula (IV-A) or (IV-B)

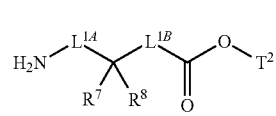

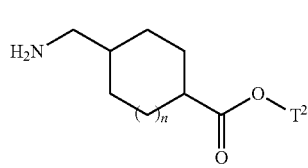

and the resulting compound of the formula (V-A) or (V-B)

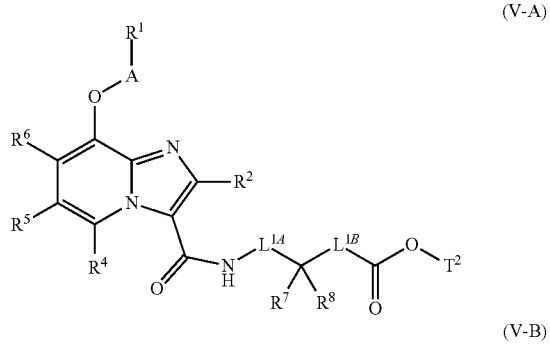

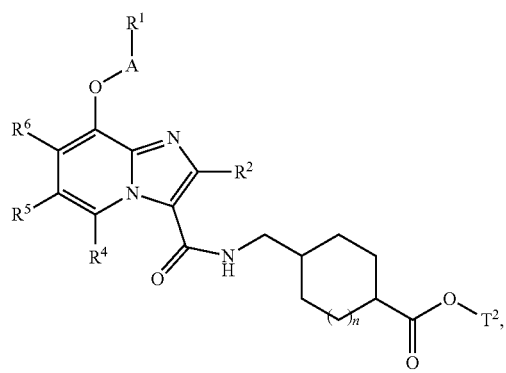

in which A, n, $R^1$, $R^2$, $R^4$, $R^5$, $R^6$, $L^{1A}$, $L^{1B}$, $R^7$ and $R^8$ each have the meanings given above
and
$T^2$ represents ($C_1$-$C_6$)-alkyl,
is optionally reacted in an inert solvent in the presence of a base or acid to give a carboxylic acid of the formula (VI-A) or (VI-B)

(VI-A)

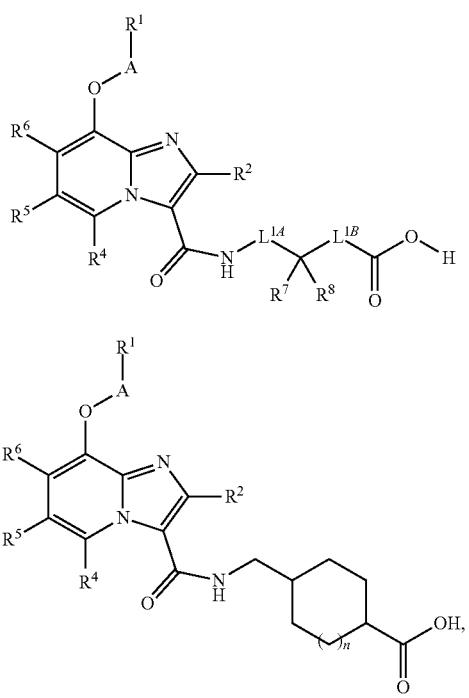

(VI-B)

or

[B] reacting a compound of the formula (III-B)

(III-B)

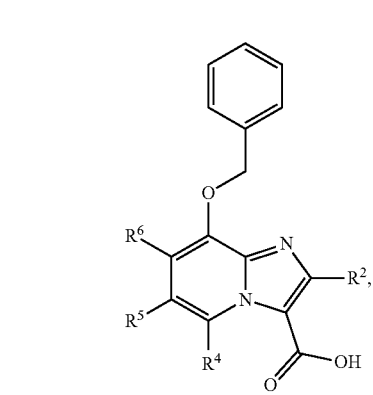

in which $R^2$, $R^4$, $R^5$ and $R^6$ each have the meanings given above, in an inert solvent under amide coupling conditions with an amine of the formula (IV-A) or (IV-B) to give a compound of the formula (V-C) or (V-D), (V-C)

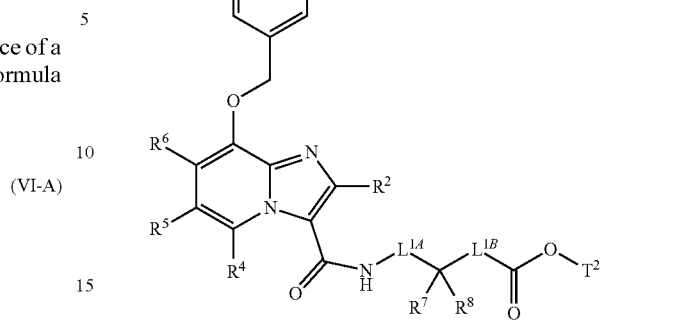

(V-D)

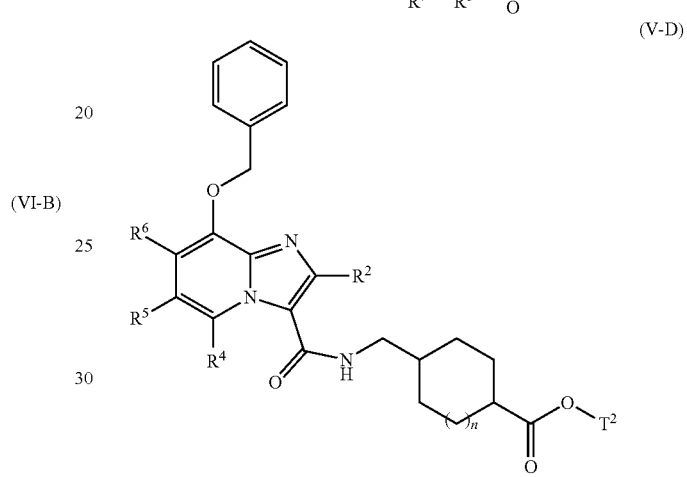

in which n, $R^2$, $R^4$, $R^5$, $R^6$, $L^{1A}$, $L^{1B}$, $R^7$ and $R^8$ each have the meanings given above, and
$T^2$ represents ($C_1$-$C_6$)-alkyl,
removing the benzyl group from the compound of formula (V-C) or (V-D) using methods known to the person skilled in the art and the resulting compound of formula (VII-A) or (VII-B)

(VII-A)

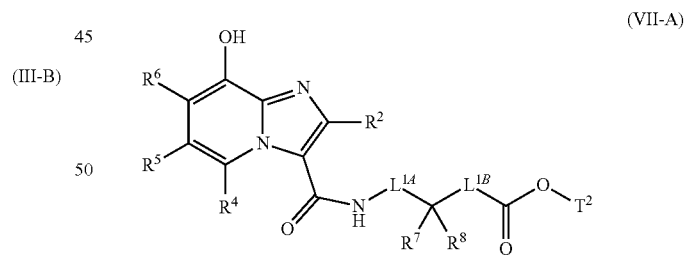

(VII-B)

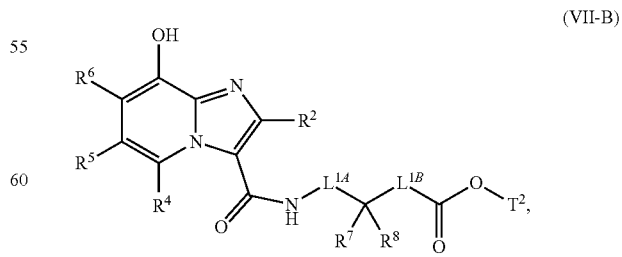

in which n, $R^2$, $R^4$, $R^5$, $R^6$, $L^{1A}$, $L^{1B}$, $R^7$ and $R^8$ each have the meanings given above, and
$T^2$ represents ($C_1$-$C_6$)-alkyl, reacting the compound of formula (VII-A) or (VII-B) in an inert solvent in the presence of a suitable base with a compound of formula (VIII)

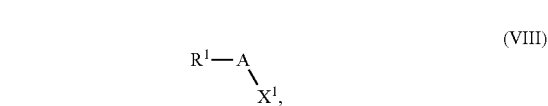

in which A and R¹ have the meanings given above and X¹ represents a suitable leaving group, in particular chlorine, bromine, iodine, mesylate, triflate or tosylate, and the compounds (V-A) or (V-B) resulting therefrom

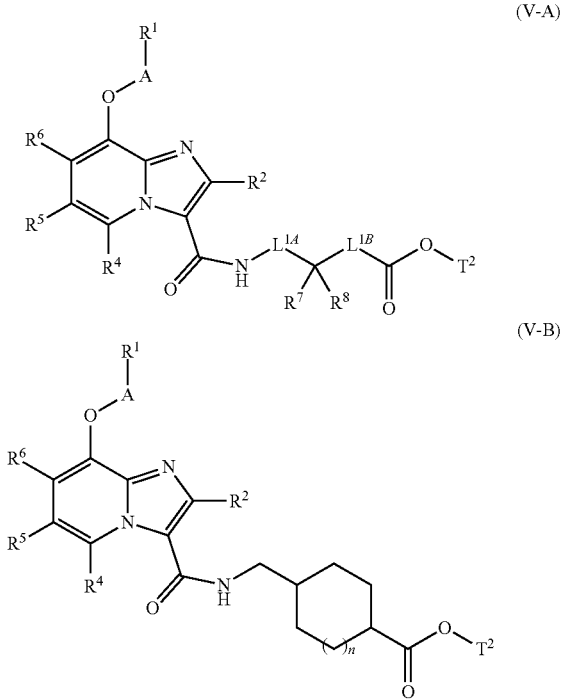

in which A, R¹, R², R⁴, R⁵, R⁶, $L^{1A}$, $L^{1B}$, R⁷ and R⁸ each have the meanings given above, and
T² represents ($C_1$-$C_6$)-alkyl, and the compound of formula (V-A) or (V-B) in an inert solvent in the presence of a suitable base or acid to give a carboxylic acid of the formula (VI-A) or (VI-B)

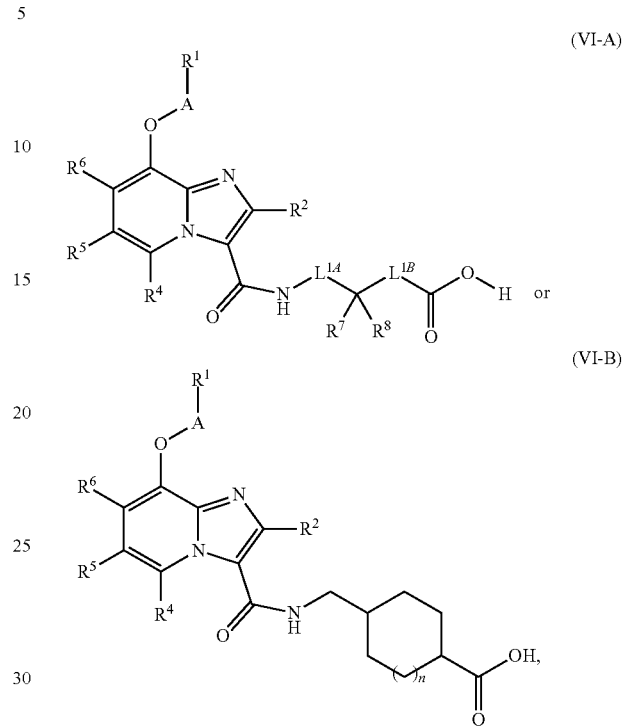

and optionally converting the resulting compounds of formula (I) with the appropriate (i) solvents and/or (ii) acids or bases into a solvates, salts and/or solvate of a salt thereof.

5. A pharmaceutical composition, comprising a compound of claim 1 and an inert, non-toxic, pharmaceutically suitable auxiliary.

6. The pharmaceutical composition of claim 5, further comprising an active compound selected from the group consisting of an organic nitrate, an NO donor, a cGMP-PDE inhibitor, an agent having antithrombotic activity, an agent lowering blood pressure, and an agent altering lipid metabolism.

* * * * *